United States Patent
Bregman et al.

(10) Patent No.: US 11,918,238 B2
(45) Date of Patent: Mar. 5, 2024

(54) CAPITAL FRAGMENT GUIDE AND RELATED METHODS

(71) Applicant: Crossroads Extremity Systems, LLC, Memphis, TN (US)

(72) Inventors: Peter Bregman, Las Vegas, NV (US); Chad Hollis, Collierville, TN (US); Tony Melkent, Germantown, TN (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 115 days.

(21) Appl. No.: 17/741,316

(22) Filed: May 10, 2022

(65) Prior Publication Data
US 2022/0354513 A1 Nov. 10, 2022

Related U.S. Application Data

(60) Provisional application No. 63/186,720, filed on May 10, 2021.

(51) Int. Cl.
*A61B 17/17* (2006.01)
*A61B 17/00* (2006.01)
*A61B 17/56* (2006.01)

(52) U.S. Cl.
CPC .......... *A61B 17/1775* (2016.11); *A61B 17/17* (2013.01); *A61B 17/1796* (2013.01); *A61B 2017/0042* (2013.01); *A61B 2017/565* (2013.01)

(58) Field of Classification Search
CPC .. A61B 17/1775; A61B 17/1796; A61B 17/17
See application file for complete search history.

(56) References Cited

U.S. PATENT DOCUMENTS

| | | | |
|---|---|---|---|
| 6,391,031 B1 * | 5/2002 | Toomey | A61B 17/15 606/82 |
| 2014/0188139 A1 | 7/2014 | Fallin et al. | |
| 2018/0110530 A1 * | 4/2018 | Wagner | A61B 17/8061 |
| 2019/0125418 A1 * | 5/2019 | Muller | A61B 17/1775 |
| 2020/0205844 A1 | 7/2020 | Hissong et al. | |
| 2021/0022879 A1 | 1/2021 | Hollis et al. | |
| 2021/0038260 A1 | 2/2021 | Hollis et al. | |
| 2021/0251670 A1 * | 8/2021 | Sayger | A61B 17/8866 |
| 2021/0369287 A1 * | 12/2021 | Boffeli | A61B 17/66 |
| 2022/0313283 A1 * | 10/2022 | Kubacki | A61B 17/1775 |

* cited by examiner

*Primary Examiner* — Christian A Sevilla
(74) *Attorney, Agent, or Firm* — BakerHostetler

(57) ABSTRACT

A capital fragment guide is configured to be temporarily secured to a capital fragment of a metatarsal that has been surgically separated from a proximal portion of the metatarsal. The capital fragment guide can be manipulated to correspondingly manipulate the capital fragment, thereby correcting a bunion. An implant can permanently secure the proximal portion to the capital fragment.

20 Claims, 29 Drawing Sheets

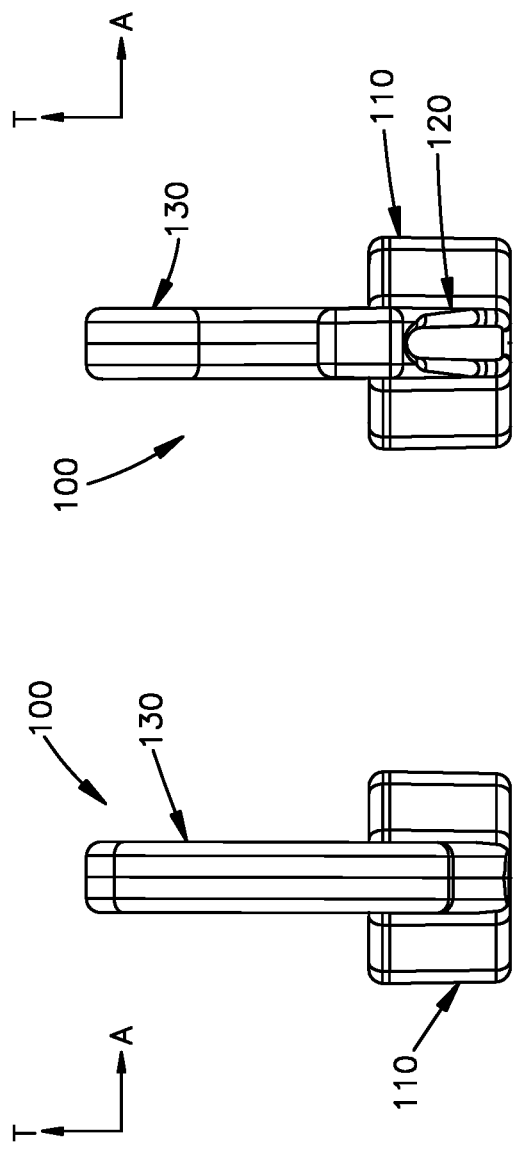
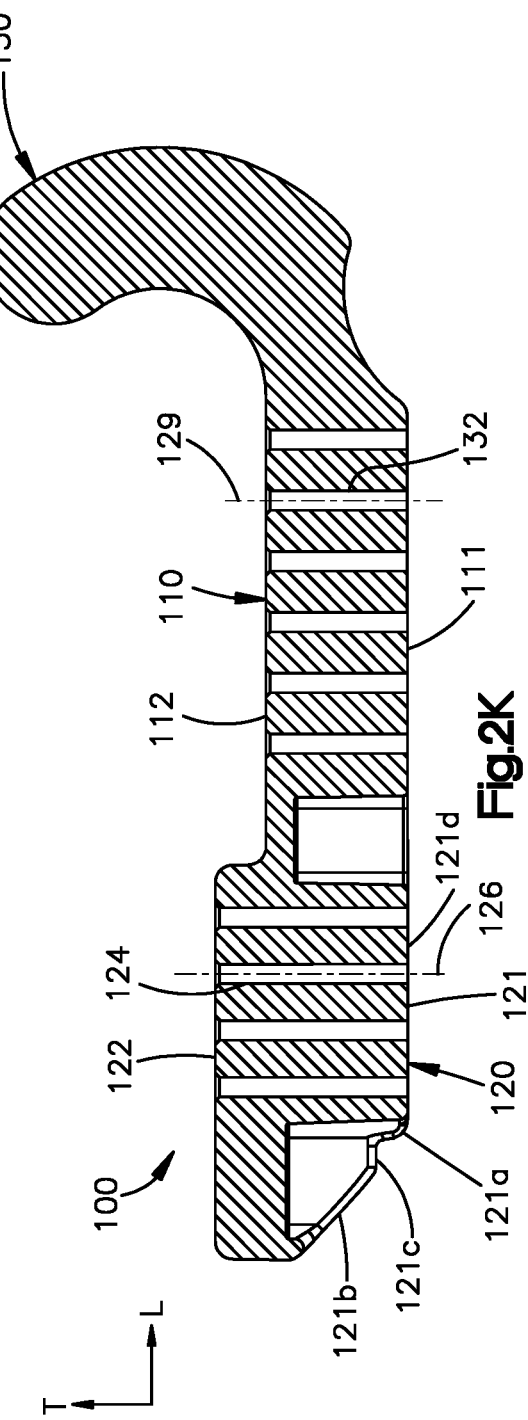

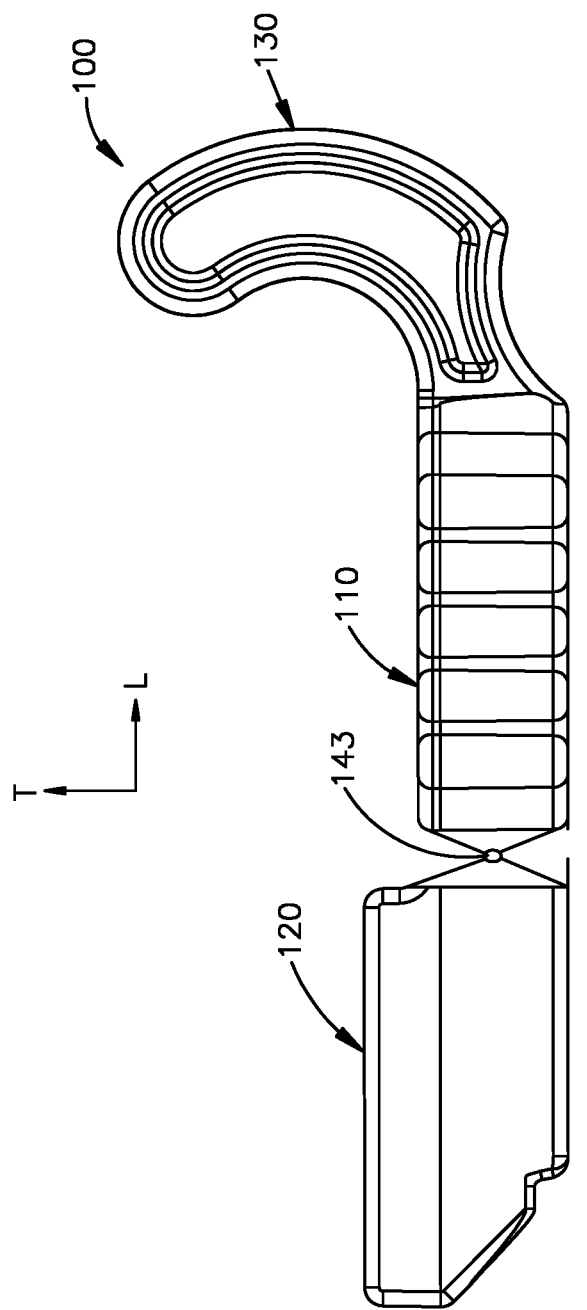

CAPITAL FRAGMENT GUIDE AND RELATED METHODS

CROSS-REFERENCE TO RELATED APPLICATIONS

This claims priority to U.S. patent application Ser. No. 63/186,720 filed May 10, 2021, the disclosure of which is hereby incorporated by reference as if set forth in its entirety herein.

BACKGROUND

Field

The present disclosure relates to surgical apparatus and methods of treatment of deformities of the foot through minimally invasive bunion correction.

Related Art

Bunions are a progressive disorder typically beginning with a leaning of the great toe, which may gradually change the angle of the bones and produce a characteristic bump on the medial side of the metatarsal near the joint of the metatarsal with the proximal phalanx. Specifically, the bunion is the prominence made of bone and at times an inflamed bursa. Hallux valgus is the condition in which the great toe deviates from the normal position toward the direction of the second toe.

Bunion correction or repair is a common surgery with over 100,000 surgeries performed annually in the U.S. Many surgical procedures for bunion repair are invasive and painful, requiring an incision of several inches and a long period of convalescence, of up to 10-12 weeks. Minimally invasive surgery has been performed in orthopedics for decades.

What is needed is an improvement to current minimally invasive surgical methods and apparatus.

SUMMARY

In one example, a guide is configured to adjust a bone having a first portion and a second portion that has been surgically separated from the first portion. The guide can include a body portion that defines a bone-facing inner surface and an outer surface opposite the inner surface. The guide can define a plurality of body portion apertures that extend through the body portion from the outer surface to the inner surface. The guide further includes an alignment portion that extends from the body portion, the alignment portion defining a respective bone-facing inner surface and a respective outer surface opposite the respective inner surface. The guide can define a plurality of alignment apertures that extend through the alignment portion from the respective outer surface to the respective inner surface. The guide can include a handle portion that extends from the body portion, such that the alignment portion and the handle portion extend from opposite ends of the body portion. The guide can be sized such that at least one of the alignment apertures is aligned with the first portion of the bone, such that at least one of the alignment apertures is configured to receive a temporary distal fixation device that is inserted into the second portion of the bone. The guide can further be sized to align least one of the body portion apertures with the first portion while the at least one of the alignment apertures is aligned with the second portion, such that at least one of the body portion apertures is configured to receive a temporary proximal fixation device that is inserted into the first portion.

The above and other features, elements, characteristics, steps, and advantages of the present invention will become more apparent from the following detailed description of the embodiments of the present invention with reference to the attached drawings.

BRIEF DESCRIPTION OF THE DRAWINGS

FIG. 2I is a rear elevation view of the capital fragment guide of FIG. 1;

FIG. 2J is a front elevation view of the capital fragment guide of FIG. 1;

FIG. 2K is a sectional side elevation view of the capital fragment guide taken along the line 2K-2K of FIG. 2G;

FIG. 12D is a side elevation view of a capital fragment guide constructed in accordance with an alternative embodiment;

Various examples are depicted in the accompanying drawings for illustrative purposes, and should in no way be interpreted as limiting the scope of the examples. Various features of different disclosed examples can be combined to form additional examples, which are part of this disclosure.

DETAILED DESCRIPTION

The various features and advantages of the systems, devices, and methods of the technology described herein will become more fully apparent from the following description of the examples illustrated in the figures. These examples are intended to illustrate the principles of this disclosure, and this disclosure should not be limited to merely the illustrated examples. The features of the illustrated examples can be modified, combined, removed, and/or substituted as will be apparent to those of ordinary skill in the art upon consideration of the principles disclosed herein.

This disclosure is directed to a capital fragment guide 100 that is configured to be temporarily fixed to a capital fragment of a first metatarsal that has been resected from a proximal portion of the metatarsal. Thus, movement of the capital fragment guide correspondingly moves the capital fragment with respect to the proximal portion, for instance to correct a bunion. The capital fragment guide can be subsequently temporarily fixed to the proximal portion to positionally fix the capital fragment with respect to the proximal portion. A permanent implant can be fixed to the proximal portion and the capital fragment, and the capital fragment guide can be removed.

Figure 1:
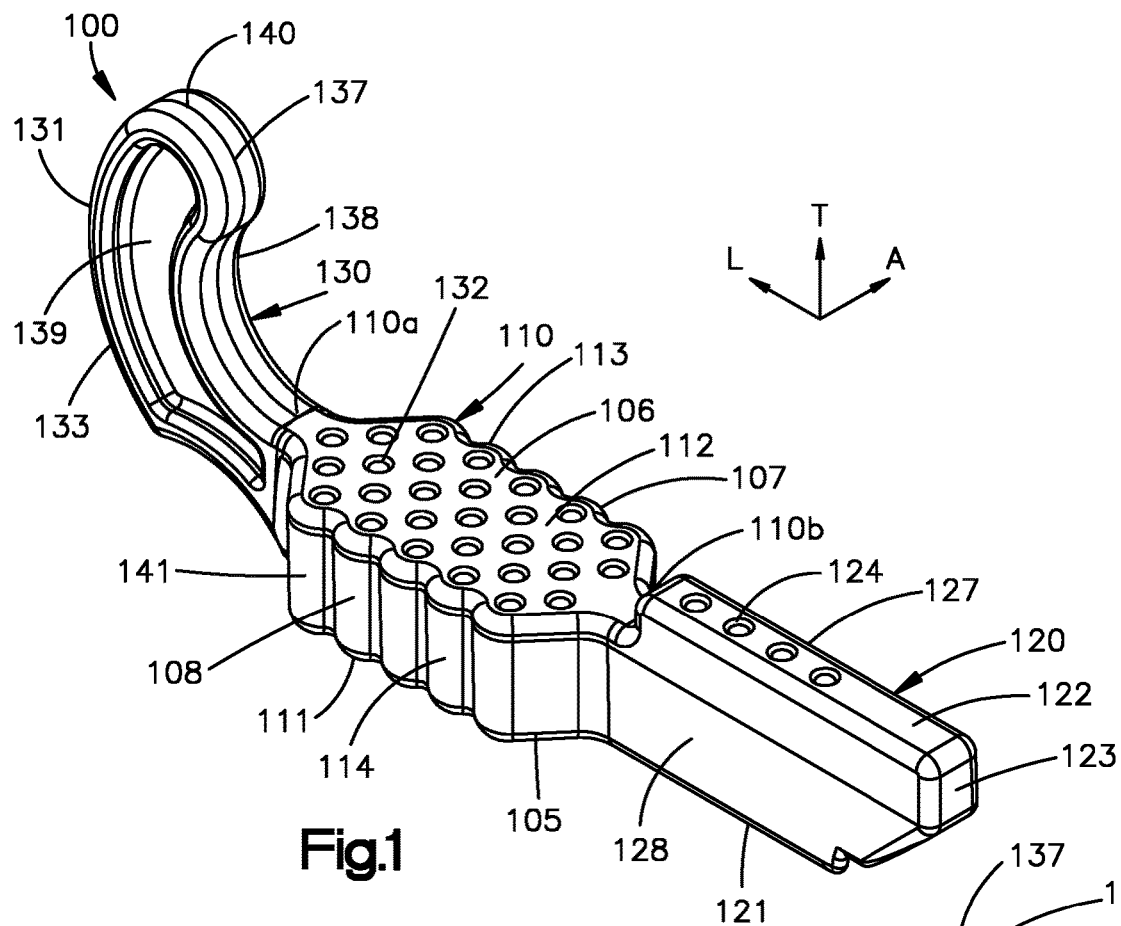
FIG. 1 is a front, top, right perspective view a capital fragment guide constructed in accordance with one example.
Figure 2A:
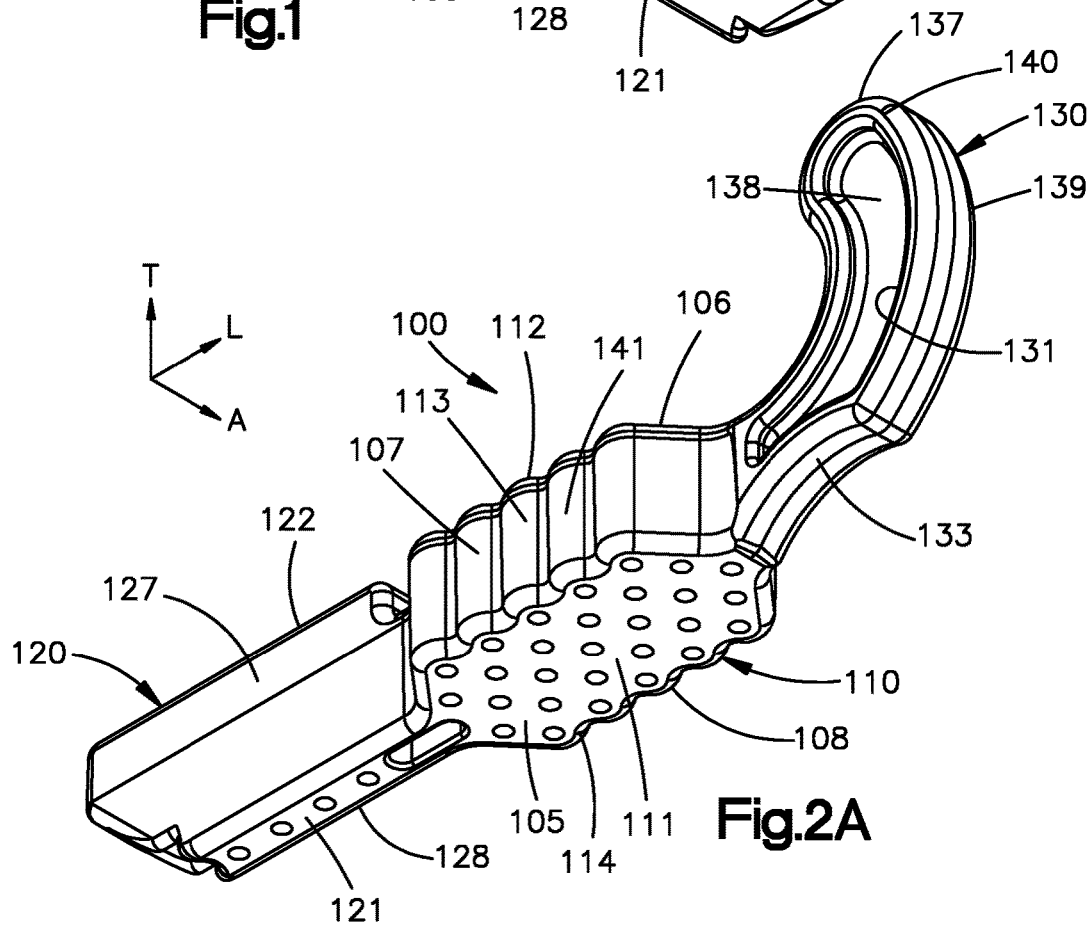
FIG. 2A is a rear, bottom, left perspective view of the capital fragment guide of FIG. 1.
Figure 2B:
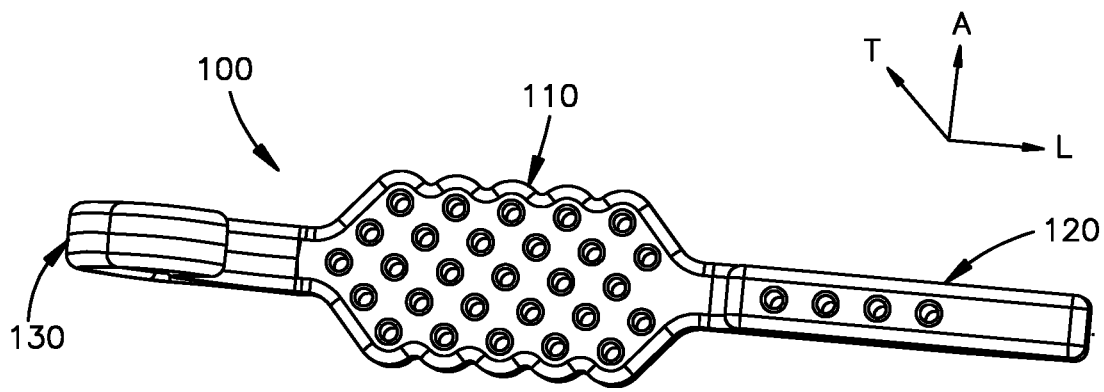
FIG. 2B is another front, top, right perspective view of the capital fragment guide of FIG. 1.
Figure 2C:
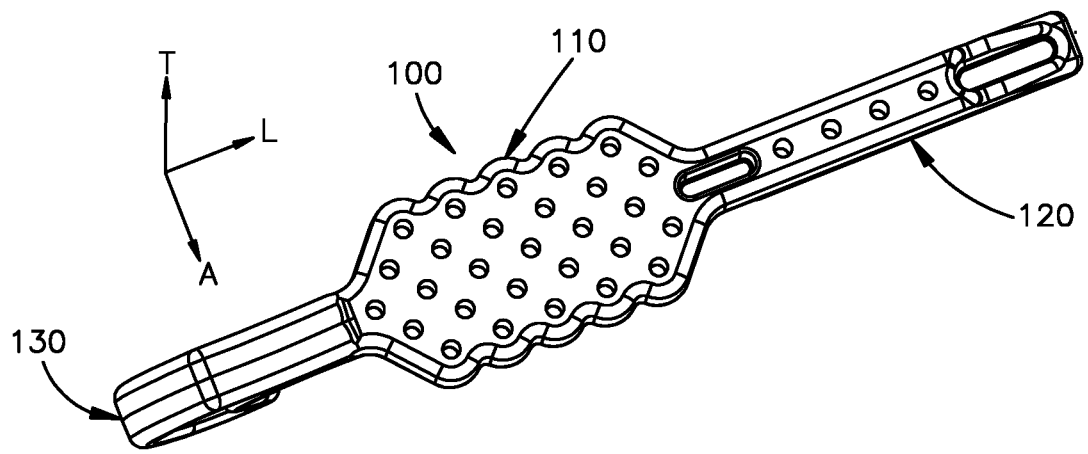
FIG. 2C is another rear, bottom, left perspective view of the capital fragment guide of FIG. 1.
Figure 2D:
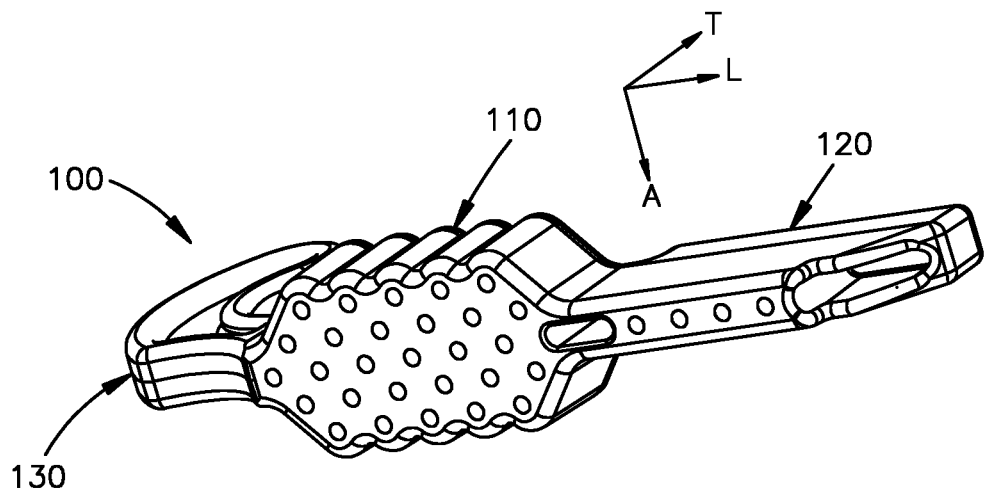
FIG. 2D is a front, bottom, right perspective view of the capital fragment guide of FIG. 1.
Figure 2E:
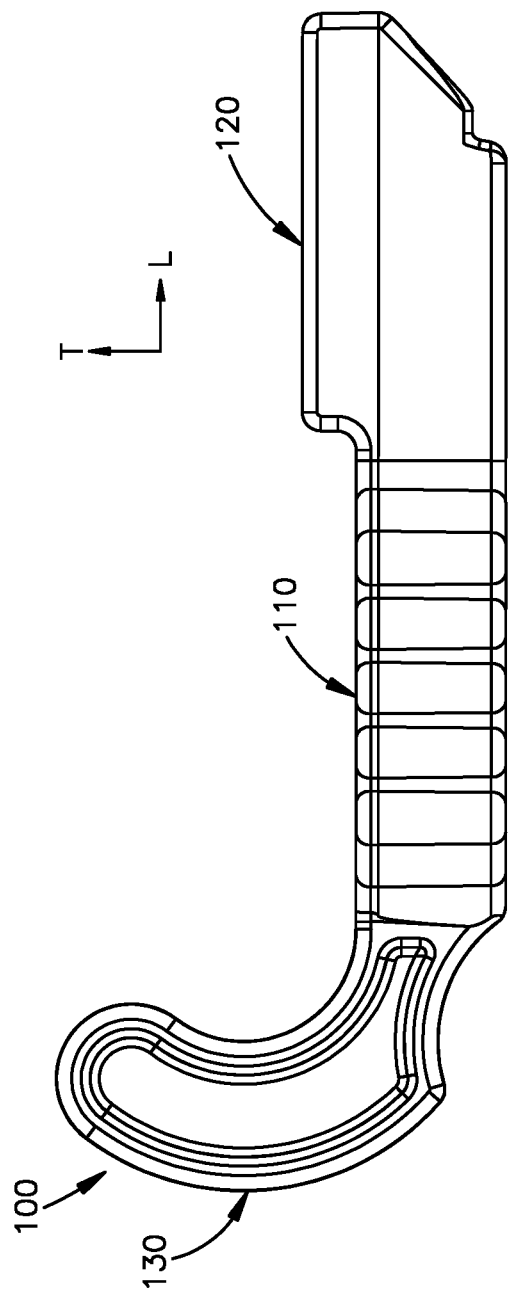
FIG. 2E is a right side elevation view of the capital fragment guide of FIG. 1.
Figure 2F:
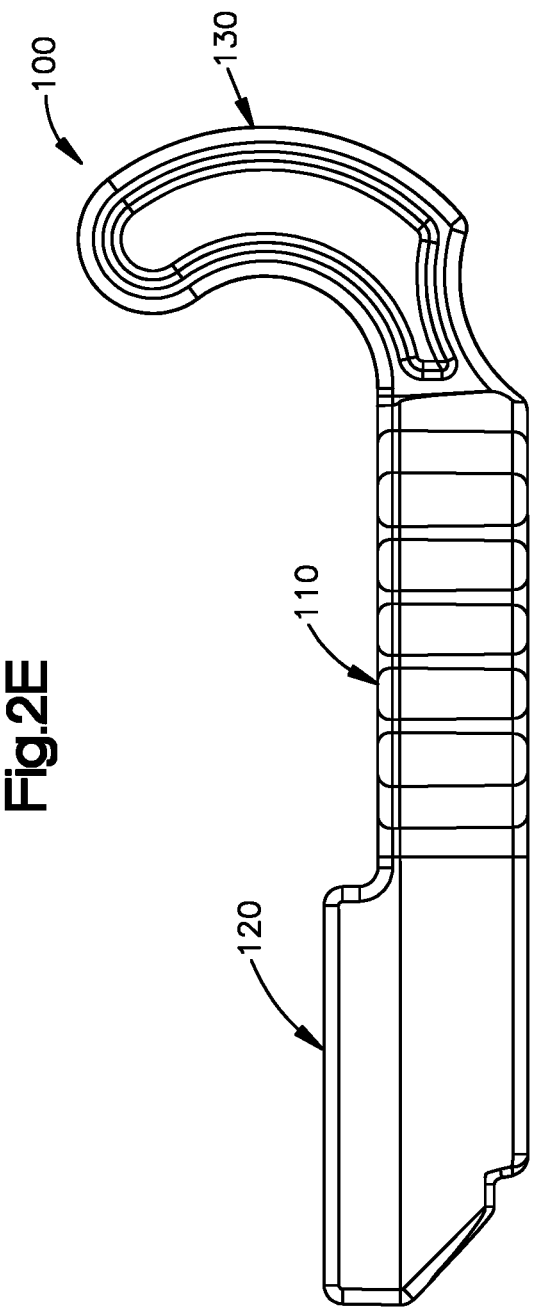
FIG. 2F is a left side elevation view of the capital fragment guide of FIG. 1.
Figure 2G:
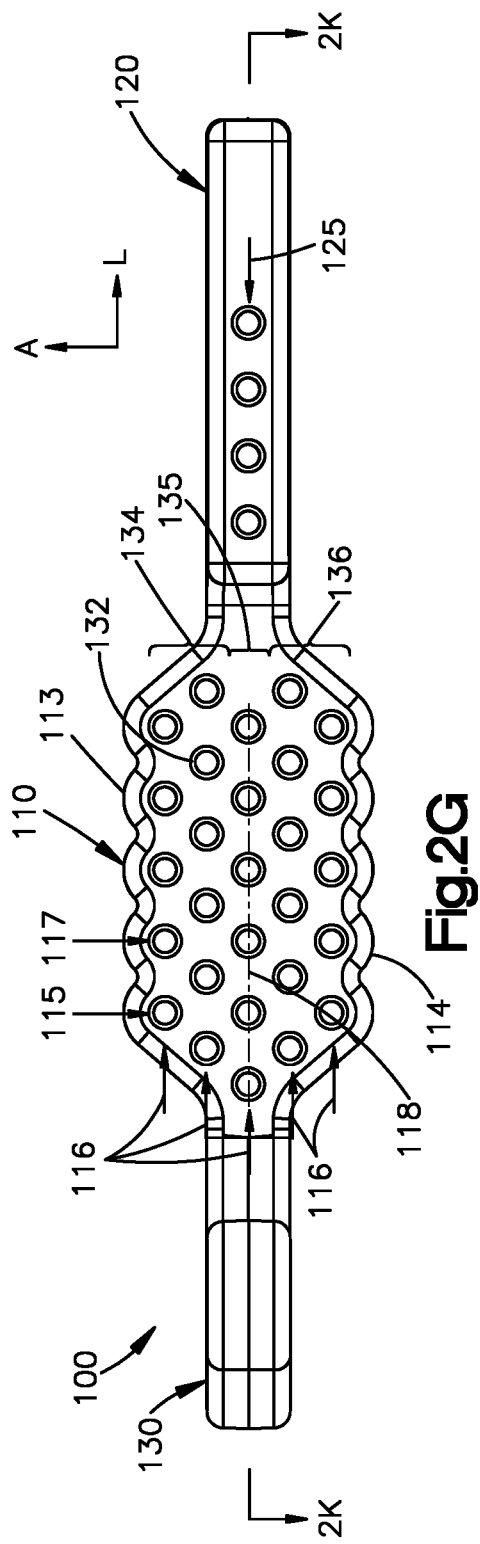
FIG. 2G is a top plan view of the capital fragment guide of FIG. 1.
Figure 2H:
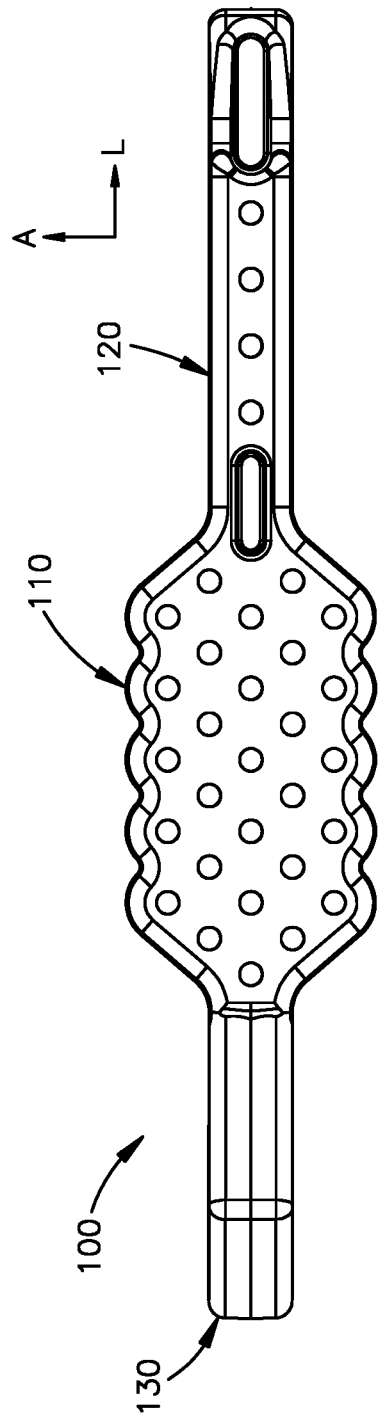
FIG. 2H is a bottom plan view of the capital fragment guide of FIG. 1.

Referring now to FIGS. 1-2K, and primarily to FIGS. 1, 2G, and 2K, a surgical system can include a capital fragment guide 100. Other components of the surgical system are described below, which can be provided as a kit, or separately provided as desired. The capital fragment guide 100 can be formed of a unitary material such aluminum, plastic, steel, or other materials suitable for use in an antiseptic surgical environment. The capital fragment guide 100 can include a body portion 110, an alignment portion 120 that extends from the body portion 110, and a handle portion 130 that extends from the body portion 110. In one example, the alignment portion 120 and the handle portion 130 can extend from opposite ends of the body portion 110. The alignment portion 120 and the handle portion 130 can extend from the body portion 110 along respective directions of elongation that are at least approximately parallel to each other in one example. Alternatively, the directions of elongation of the alignment portion 120 and the handle portion 130 can be angularly offset to each other as desired.

The body portion 110 defines a first or proximal end 110a and a second or distal end 110b opposite the proximal end 110a along a longitudinal direction L. A "distal direction" and derivatives thereof can thus be defined as a direction from the proximal end 110a to the distal end 110b. Conversely, a "proximal direction" and derivatives thereof can be defined as a direction from the distal end 110b to the proximal end 110a. The proximal direction and the distal direction can each extend along the longitudinal direction L. The alignment portion 120 and the handle 130 can define opposed terminal ends of the capital fragment guide 100. For instance, the alignment portion 120 can define a distal end of the capital fragment guide 100, and the handle 130 can define a proximal end of the capital fragment guide 100.

As will be appreciated from the description below, the distal end 110b can be spaced from the proximal end 110a in an anatomical distal direction when placed against the first metatarsal. In one example, the alignment portion 120 can extend distally from the distal end 110b of the body portion 110, and the handle portion 130 can extend proximally from the proximal end 110a of the body portion 110. The capital fragment guide 100, including the body portion 110, the alignment portion 120, and the handle portion 130, will now be described in more detail.

The capital fragment guide 100 defines a bone-facing inner surface 105 that is configured to face an underlying metatarsal, and an outer surface 106 that is opposite the inner surface 105 along the transverse direction T that is perpendicular to the longitudinal direction L. The inner surface 105 can be at least partially defined by a bone-facing inner surface 111 of the body portion 110 that is configured to face the underlying metatarsal, and a bone-facing inner surface 121 of the alignment portion 120 that is configured to face the underlying metatarsal. In some examples, the inner surface 105 of the capital fragment guide can be further defined by an inner surface 133 of the handle portion 130. The outer surface 106 of the capital fragment guide 100 can be at least partially defined by an outer surface 112 of the body portion 110 that is opposite the inner surface 111 along the transverse direction T, and an outer surface 122 of the alignment portion that is opposite the inner surface along the transverse direction T. In some examples, the outer surface 106 of the capital fragment guide 100 can be further defined by an outer surface 137 of the handle portion 130 that is opposite the inner surface 133 along the transverse direction T. Thus, the inner surface 105 and the outer surface 106 can extend along each of the body portion 110, the alignment portion 120, and the handle portion 130.

The capital fragment guide 100 can further include first and second external sides 107 and 108 that are opposite each other along a lateral direction A that is perpendicular to each of the longitudinal direction L and the transverse direction T. For instance, the first external side 107 can be spaced from the second external side 108 along a first lateral direction that extends along the lateral direction A. Conversely, the second external side 108 can be spaced from the first external side 107 along a second lateral direction that is opposite the first lateral direction, and thus also extends along the lateral direction A. The first and second external sides 107 and 108 extend from the inner surface 105 to the outer surface 106. The first external side 107 can be at least partially defined by a first external side 113 of the body portion 110 and a first external side 127 of the alignment portion 120. The first external side 107 can further be partially defined by a first external side 138 of the handle portion 130. The second external side 108 can be at least partially defined by a second external side 114 of the body portion 110 and a second external side 128 of the alignment portion 120. The second external side 108 can further be partially defined by a second external side 139 of the handle portion 130. Thus, the first and second external sides 107 of the capital fragment guide 100 can extend along each of the body portion 110, the alignment portion 120, and the handle portion 130. In this regard, the first external sides 113, 127, and 138 of the body portion 110, the alignment portion 120, and the handle portion 130, respectively, can be spaced along the first lateral direction from the second external sides 114, 128, and side 139, of the body portion 110, the alignment portion 120, and the handle portion 130, respectively.

The body portion 110 can have a width from the first external side 113 to the second external side 114 along the lateral direction A that is in a range from approximately 0.75 inch to approximately 2 inches. It is appreciated that in certain implementations, the body portion 110 can include a wider or narrower width depending on the number of situations that particular guide is designed to be used in. In one example, the width of the body portion 110 can be greater than the width of either or both of the alignment portion 120 and the handle portion 130 from their respective first external sides to their respective second external sides along the lateral direction A.

The capital fragment guide 100 can include a plurality of body portion apertures 132 that extend through the body portion 110. As will be appreciated from the description below, the body portion apertures 132 can receive temporary fixation devices such as Kirschner wires (K-wires) that positionally fix the capital fragment guide 100 to a proximal portion of a metatarsal. The surgeon can select those apertures 132 that are to receive temporary fixation devices based, for instance, on alignment with bone of the underlying proximal portion that can reliably receive the temporary fixation device.

The apertures 132 can extend from the outer surface 112 to the inner surface 111 of the body portion 110 as through-holes. The apertures 132 can extend along respective straight linear central axes 129 from the outer surface 112 to the inner surface 111. Either or both of the outer surface 112 and the inner surface 111 can be planar surfaces as desired. Further, the outer surface 112 and the inner surface 111 can be parallel to each other. The apertures 132 can be arranged in a structured pattern such as an array 115. The array 115 can be defined by a plurality of columns 116 of one or more apertures 132 that are spaced from each other along the lateral direction A. The apertures 132 of each column 116 can be aligned with each other along the longitudinal direction L. Further, the apertures 132 of adjacent columns 116 can be offset with respect to each other along the lateral direction A. The array 115 can further be defined by a plurality of rows 117 of one or more apertures 132. The rows 117 can be oriented perpendicular to the columns 116. For instance, the rows 117 can be oriented along the lateral direction A and spaced from each other along the longitudinal direction L. The array 115 can include more rows 117 than columns 116 in some examples. It should be appreciated, of course, that the apertures 132 can be disposed in any suitable alternative array as desired, patterned or not.

The body portion apertures 132 can be organized into various sections, including a central section 135, a first side section 134, and a second side section 136. The central section 135 can include one or more of the apertures 132 aligned on a centerline 118 of the body portion 110. The centerline 118 can extend along the longitudinal direction L, and can bisect the body portion 110 equidistantly between the first external side 113 and the second external side 114. In one example, the central axes 129 of the one or more apertures 132 of the central section 135 can intersect the centerline 118 in one example. While the central section 135 can include a single one of the columns 116 aligned with the centerline 118 in some examples, it should be appreciated that the central section 135 can alternatively include one or columns 116 that are adjacent the centerline, such as columns 116 that are disposed on opposite sides of the centerline 118.

The first side section 134 can be disposed between the central section 135 and the first external side 113. Thus, the one or more apertures 132 of the first side section 134 can be offset toward the first external side 113 with respect to the one or more apertures 132 of the central section 135. The second side section 136 can be disposed between the central section 135 and the second external side 114. Thus, the one or more apertures 132 of the second side section 136 can be offset toward the second external side 114 with respect to the one or more apertures 132 of the central section 135.

In one example, the inner and outer surfaces 111 and 112 of the body portion 110 can be planar along a plane that is perpendicular to the transverse direction T. Alternatively, the inner and outer surfaces 111 and 112 of the body portion 110 can be planar along a plane that is angularly offset with respect to the transverse direction T. The respective central axes 129 of one or more up to all of the apertures 132 can be oriented normal to either or both of the inner and outer surfaces 111 and 112, respectively. In other examples, the central axes 129 of one or more up to all of the apertures 132 can define a non-perpendicular angle with respect to either or both of the inner and outer surfaces 111 and 112, respectively. The non-perpendicular angle can be the same for all apertures 132 or different for one or more apertures 132 with respect to the other apertures 132. A non-perpendicular angle of a given central axis 129 with respect to the inner and outer surfaces 111 and 112 can be measured in any plane that includes the given central axis 129.

In another example, the inner and outer surfaces 111 and 112 of the body portion 110 can be nonplanar as desired. The respective central axes 129 of one or more up to all of the apertures 132 can be oriented substantially parallel to the transverse direction T. In other examples, the central axes 129 of one or more up to all of the apertures 132 can define an angle with respect to the transverse direction T. The angle can be the same for all apertures 132 or different for one or more apertures 132 with respect to the other apertures 132. The angle can be measured in any plane that includes the transverse direction T.

It should thus be appreciated that the central axes 129 of all of the apertures 132 can be parallel to each other in some examples. In other examples, the central axes 129 of one or more of the apertures 132 can be angularly offset with respect to the central axes 129 of one or more others of the apertures 132 as desired. For instance, the central axes 129 of the apertures 132 in each section can be parallel to each other, and angularly offset with respect to the central axes 129 of the apertures 132 of another section. Alternatively or additionally, the central axes 129 of the apertures 132 in each column 116 can be parallel to each other, and angularly offset with respect to central axes 129 of the apertures 132 of another column 116. Alternatively or additionally still, the central axes 129 of the apertures 132 in each row 117 can be parallel to each other, and angularly offset with respect to the central axes 129 of the apertures 132 of another row 117. In still other examples the central axis 129 of at least one aperture 132 of a given section, column 116, and/or row 117 can be angularly offset with respect the central axis 129 of at least one other aperture 132 the given section, column 116, and/or row 117.

With continuing reference to FIGS. 1-2K, and as described above, the guide 100 can include an alignment portion 120 that extends out with respect to the body portion 110. For instance, the alignment portion 120 can extend distally from the distal end 110b of the body portion 110. In one example, the alignment portion 120 can define a monolithic unitary structure with the body portion 110. Alternatively, the alignment portion 120 can be discrete and secured to the body portion 110. The alignment portion 120 extends from body portion 110 to a free terminal end 123. The alignment portion 120 can be generally aligned along the center line 118 of the body portion 110.

The capital fragment guide 100 can include a plurality of alignment apertures 124 that extend through the alignment portion 120 from the outer surface 122 to the inner surface 121. The alignment portion 120 can have a height from the outer surface 122 to the inner surface 121 that is greater than the height of the guide portion 110 from the outer surface 112 to the inner surface 111. The apertures 124 can extend along respective straight linear central axes 126 from the outer surface 122 to the inner surface 121. As will be appreciated from the description below, the alignment apertures 124 can receive temporary fixation devices such as K-wires that positionally fix the capital fragment guide 100 to a capital fragment of the metatarsal. The surgeon can select those apertures 132 that are to receive temporary fixation devices based, for instance, on alignment with bone of the underlying distal fragment portion that can reliably receive the temporary fixation device. As will be described in more detail below, positional manipulation of the capital fragment guide 110, and in particular or the alignment portion 120, can cause corresponding positional manipulation the distal fragment portion with respect to the proximal portion of the metatarsal when the body portion 110 is not temporarily fixed to the proximal portion.

The plurality of alignment apertures 124 can be aligned in at least one column 125 that is oriented along the longitudinal direction L. In one example, the alignment apertures 124 are aligned in a single column 125 that is oriented along the longitudinal direction L. The column 125 can be aligned with the central section 135 of the body portion apertures 132 along the longitudinal direction L. Thus, respective central axes 126 of the alignment apertures 124 can lie on the centerline 118. It should be appreciated that the column 125 can alternatively be oriented along a direction that is angularly offset with respect to the longitudinal direction L, and thus angularly offset with respect to the central section 135 of body portion apertures 132. The apertures 124 can be aligned with each other along the column 125. Alternatively, the apertures 124 can be staggered with respect to each other along the column 125. In still other examples, the apertures 124 can be arranged in more than one column. In this regard, the apertures 124 can be arranged in any suitable array as desired.

In one example, adjacent ones of the alignment apertures 124 can be spaced apart a center-to-center distance between approximately 0.25 inch and 1.25 inches. As illustrated, the plurality of apertures 124 can include four apertures or any other number of apertures as desired. The apertures 124, and all apertures described herein as being configured to receive K-wires, can be sized relative to the k-wire intended to be received therein. In one example, the K-wires can have a diameter of 0.062 inch, and the apertures 124 can have a diameter of approximately 0.069 inch. It should be appreciated, of course, that the alignment apertures 124 and all K-wire receiving apertures described herein can be sized to receive any sized k-wire. Thus, in one examples, the apertures can have a respective diameters in a range from approximately 0.040 inch to approximately 0.125".The central axes 126 of the alignment apertures 124 can be oriented parallel with one another, and parallel with the body portion apertures 132. For instance, the central axes 126 can be oriented along the transverse direction T. Alternatively, the central axes 126 can be oriented along an angled direction that is angularly offset with respect to the transverse direction T. The angled direction can be defined in any plane that extends along the central axes 126. Further, the central axes 126 of the apertures 124 can be oriented perpendicular to either or both of the inner surface 121 and the outer surface 122.

The inner surface 121 may include one or more angled surface portions, such as a first or proximal angled surface portion 121a and a second or distal angled surface portion 121b that is spaced from the proximal angled surface portion 121a in the distal direction. In one example, the inner surface 121 can include an intermediate surface portion 121c that extends between the proximal angled surface portion 121a and the distal angled surface portion 121b. Alternatively, the distal angled surface portion 121b can extend from the proximal angled surface portion 121a. Each of the proximal and distal angled surface portions 121a and 121b can extend outward toward the outer surface 122 as they extend in the distal direction. The distal angled surface portion 121b can extend at a greater, lesser, or substantially equal angle toward the outer surface 122 compared to the proximal angled surface portion 121a. The proximal angled surface portion 121a can be curved as it extends along the longitudinal direction L. In one example, none of the alignment apertures 124 extends to the distal angled surface portion 121b. Alternatively or additionally, in one example none of the alignment apertures 124 extends to the distal angled surface portion 121b. It should be appreciated that the angled surfaces can be straight and linear or curved as desired.

The inner surface 121 can further include a third or aligned surface portion 121d that is aligned with, and thus coplanar with, the inner surface 111 of the body portion 110. The aligned surface portion 121d can be parallel with the intermediate surface portion 121c as desired. Alternatively, the third surface portion 121d can be angularly offset with respect to the inner surface 111. The aligned surface portion 121d can extend distally from the inner surface 111 of the body portion 110, and the proximal angled surface portion 121a can extend distally from the aligned surface portion 121c. All of the apertures 124 can extend to the aligned inner surface portion 121d in one example. Alternatively, one or more of the apertures 124 can extend to the proximal angled surface portion 121a. Alternatively or additionally, one or more of the apertures 124 can extend to the distal angled surface portion 121b.

The outer surface 122 of the alignment portion 120 can be extend from the outer surface 112 of the body portion 110. The outer surface 122 can be parallel with the outer surface 112 and offset with respect to the outer surface 112 in a transverse outward direction that is defined from the inner surface 111 toward the outer surface 112. Alternatively, the outer surface 122 can be angularly offset with respect to the outer surface 112. In still other examples, the outer surface 122 and the outer surface 112 can be aligned and thus coplanar with each other.

With continuing reference to FIGS. 1-2K, and as described above, the capital fragment guide 100 can include a handle portion 130 that extends from the proximal end 110a of the body portion 110. The handle portion 130 can provide at least one grip section 131 configured to be grasped by the surgeon so as to positionally manipulate the capital fragment guide 100. The grip section 131 can define greater frictional forces with the surgeon's hand with respect to other sections of the handle portion 130. In particular, the grip section 131 can be defined at an outer perimeter of the handle portion, and can extend outward both along the first lateral direction with respect to the first external side 138 of the handle portion 130, and along the second lateral direction with respect to the second external side 139. Thus, the first and second external sides 138 and 139 can be recessed with respect to the grip section 131. The grip section 131 can be ribbed or otherwise textured as desired. The handle portion 130 can include a raised, curved knob 140 that extends outward (along a direction from the inner surface 105 toward the outer surface 106) relative to the outer surface 112 of the body portion 110. Thus, the handle portion 130 can be easier to grasp and to maneuver. The handle portion 130 and the alignment portion 120 can have respective widths along the lateral direction A that are less than that of the body portion 110. For instance, the width of the handle portion 130 can be in a range from approximately 0.25 inch to approximately 1 inch along the lateral direction A. The width of the alignment portion 120 can be substantially equal to that of the handle portion 130.

Figure 3A:
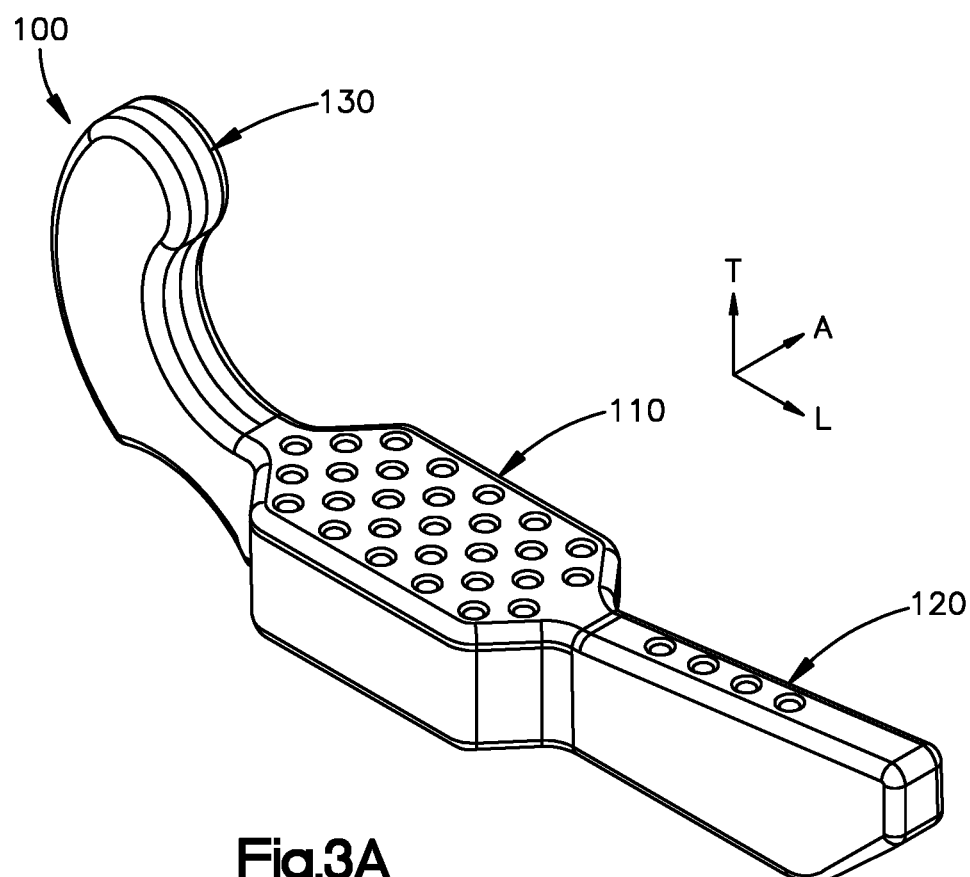
FIG. 3A is a perspective view of a capital fragment guide constructed in accordance with another example.
Figure 3B:
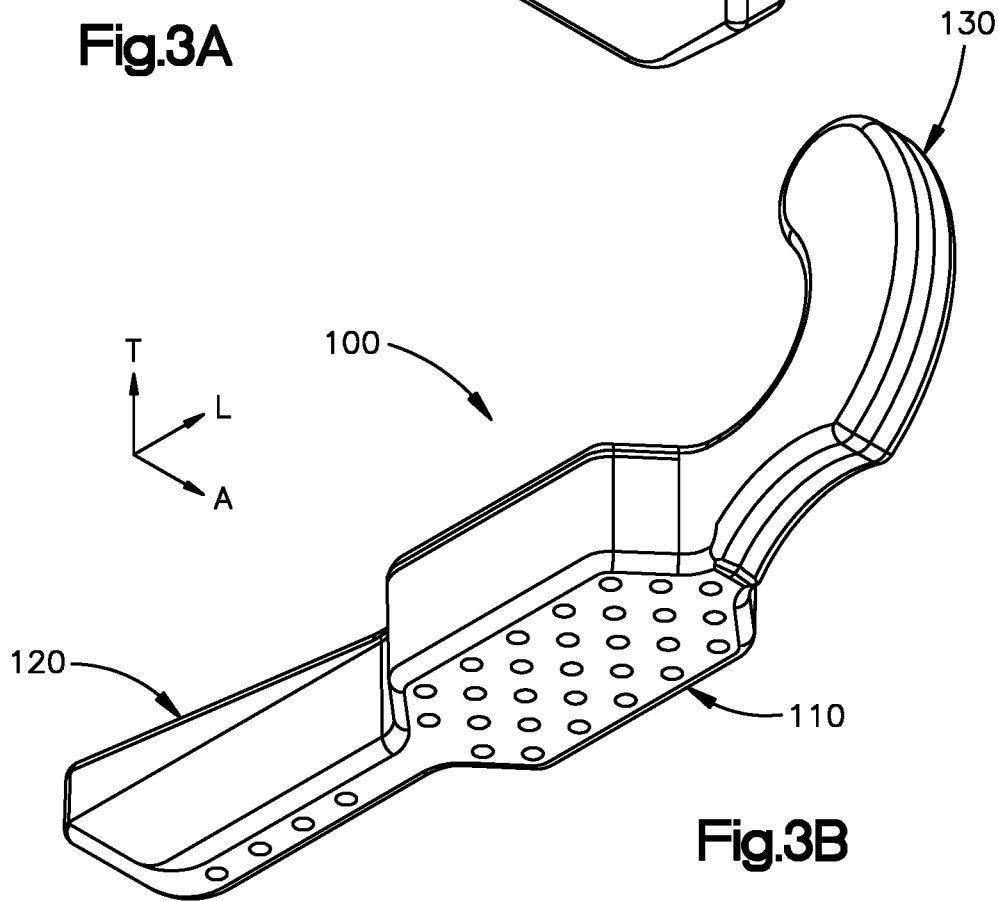
FIG. 3B is another perspective view of the capital fragment guide of FIG. 3A.

With continuing reference to FIGS. 1-2K generally, either or both of the first and second external sides 113 and 114 of the body portion 110 can include ribs 141 or other surface texture that facilitates gripping of the body portion 110 by the surgeon. The ribs 141 can be elongate along the transverse direction T, or any other direction as desired. The ribs 141 can be spaced from each other along the longitudinal direction L or any other direction as desired. As shown in FIG. 3, the first and second external sides 113 and 114 of the body portion 110 can alternatively be smooth. The grip section 131 can also terminate at position that is aligned with the first and second external sides 138 and 139 of the handle portion 130. The capital fragment guide 100 of FIG. 3 can otherwise be constructed as shown and described with reference to FIGS. 1-2K.

A surgical technique using the capital fragment guide 100 will now be described with reference to FIGS. 4A-15. With initial reference to FIG. 4A, a patient's foot 20 includes a metatarsal 22 and a proximal phalanx 24 that includes a bunion 26 or other deformity. The metatarsal 22 can be the anatomical first metatarsal. It should be appreciated that the metatarsal 22 can alternatively be any metatarsal, particularly when the proximal phalanx 24 includes a non-bunion deformity. In the illustrated example, an angle between the metatarsal 22 and the proximal phalanx 24 can form an uncomfortable bunion and hallux valgus that can be repaired using a surgical technique as presently described. The embodiments and methods herein are described largely in conjunction with surgical methods and instruments for the correction of bunions and hallux valgus. However, the instruments and methods described herein can also be used in conjunction with other portions of the body to reorient and secure bone fragments. Accordingly, the metatarsal 22 can be understood to be a first bone and the proximal phalanx 24 can be understood to be a second bone. Likewise, the metatarsal 22 that is resected and separated into a proximal portion and a distal capital fragment as described below can be understood to apply to the first bone separated into first and second portions, respectively, by the resection. Further, the capital fragment guide 100 can be referred to as a guide.

Figure 4A:
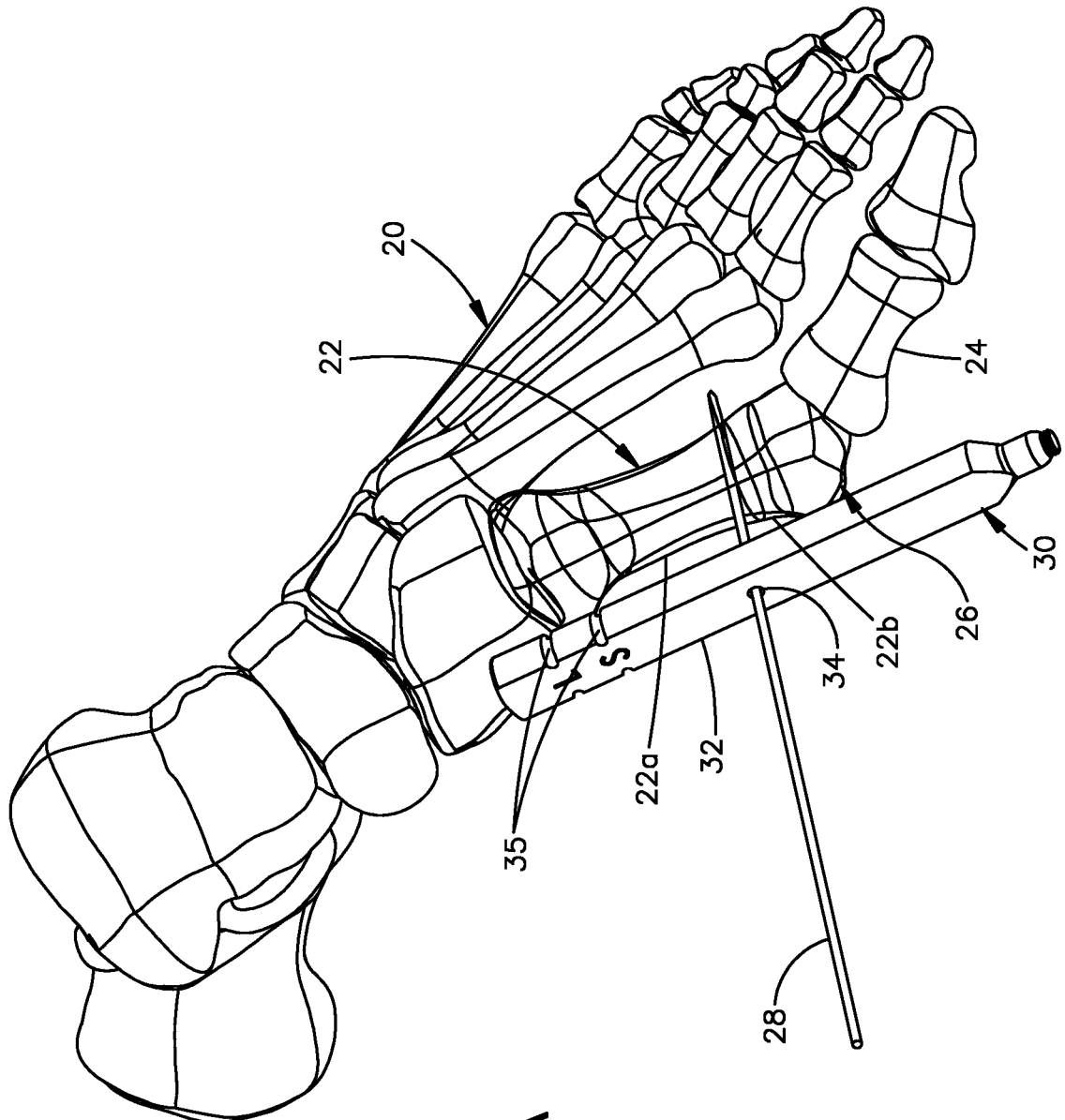
FIG. 4A is a perspective view of a first K-wire extending through a sizing guide and into a first metatarsal of a patient's foot having a bunion during a surgical bunion correction procedure.
Figure 4B:
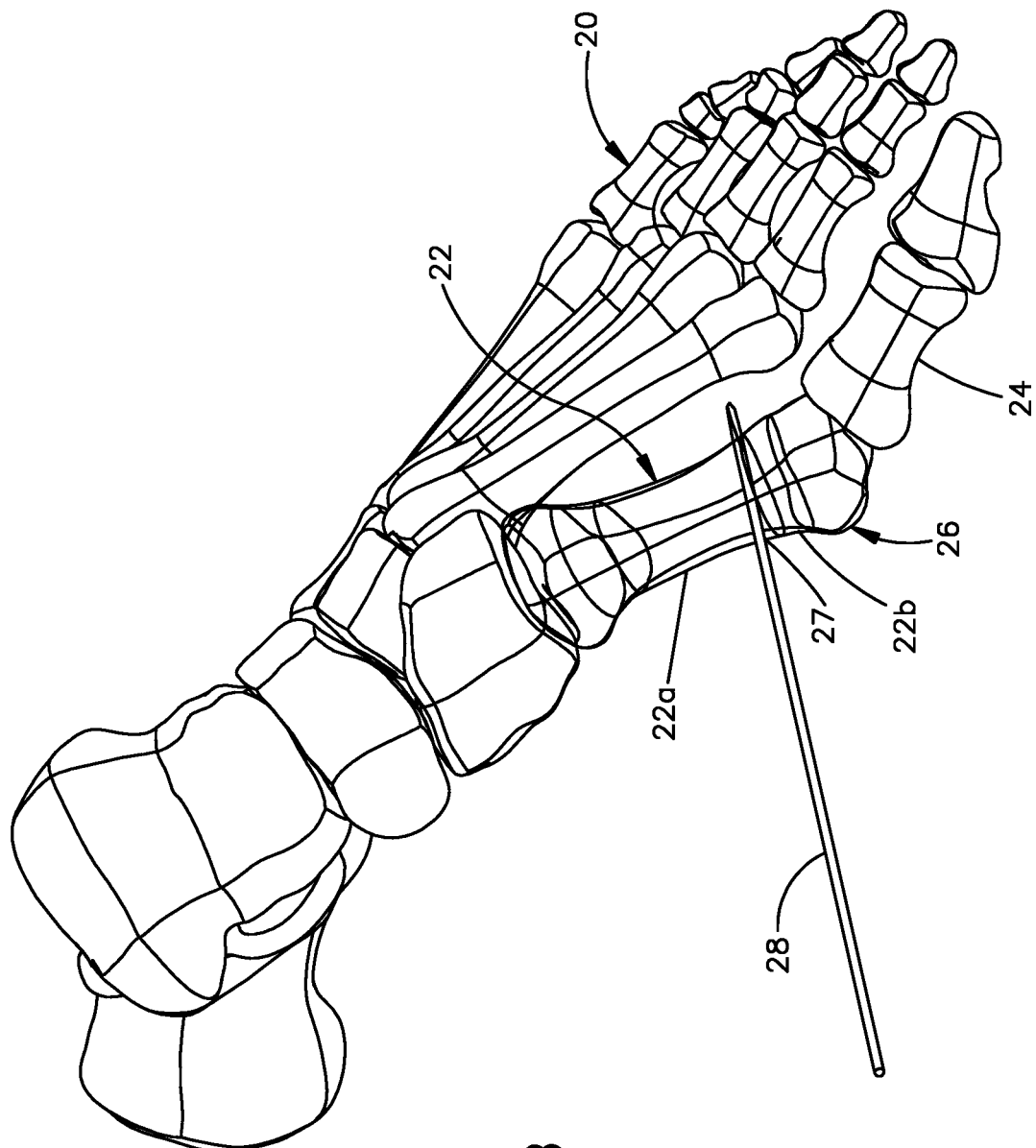
FIG. 4B is the perspective view of FIG. 4A, but showing the sizing guide removed, such that the first K-wire extends into the first metatarsal of the patient's foot.

As illustrated in FIGS. 4A-4B, the surgical system can further include a first temporary fixation device such as a first K-wire 28 that can be inserted into the metatarsal 22 at a desired position 27. As will be appreciated from the description below, the desired position 27 can be the position whereby the metatarsal will be resected. An incision can be made in the patent's skin and soft tissue, such that the first K-wire can be inserted through the incision into the metatarsal 22 at the desired position 27. The desired position 27 can coincide with a location that is earmarked to be on a cut plane that separates a proximal portion 22a of the metatarsal 22 from a distal portion 22b of the metatarsal 22. Once the distal portion 22b of the metatarsal 22 is separated from the proximal portion 22a, the distal portion 22b will define a capital fragment as is described in more detail below. In this regard, the first K-wire 28 can be referred to as a cut plane K-wire 28 or a temporary cut plane fixation device. It should be appreciated that the present disclosure can be applied to any bone in addition to the metatarsal, and thus the proximal portion 22a can be referred to as a first or proximal portion of a bone, the distal portion 22b can be referred to as a second or distal portion of the bone, and the capital fragment can be referred to as a separated second or distal portion of the bone that has been separated from the first or proximal portion of the bone.

In one example, the first K-wire 28 driven into the desired position 27 by any suitable instrument as desired. A sizing guide 30 can then be placed over the first K-wire 28 to determine a size of the proximal portion 22a that will determine a corresponding size of a permanent implant that will be installed later (see implant 52 of FIGS. 10A-10C). The sizing guide 30 can include a sizing guide body 32 and a sizing guide aperture 34 that extends through the sizing guide body 32 along a respective central axis and is sized to receive the K-wire 28. The sizing guide aperture 34 can have a diameter that is substantially equal to the diameter of the first K-wire 28, such that the first K-wire 28 is translatable in the sizing guide body 32 only along the central axis of the sizing guide aperture 34 as it travels through the sizing guide aperture 34. Thus, translation of the K-wire 28 along a direction angularly offset to the central axis of the sizing guide aperture 34, and angulation of the K-wire 28 in the sizing guide aperture 34 is substantially prevented. The sizing guide 30 can be aligned generally with the metatarsal 22, such that the sizing guide aperture 34 is aligned with the desired position 27 along a desired trajectory that is defined by the central axis of the sizing guide aperture 34. The sizing guide 30 can include two or more size indicators 35 that the surgeon can visually inspect during use to determine the proper sizing of the permanent implant.

During operation, the first K-wire 28 can be driven into the desired position 27 of the metatarsal 22 in an insertion direction. If the K-wire is threaded, the K-wire 28 can be rotated so as to threadedly purchase the first K-wire 28 with the metatarsal 22 as the K-wire travels into the metatarsal 22. Alternatively, the K-wire 28 can have a smooth outer surface that purchases with the metatarsal 22. The sizing guide 30 can subsequently be installed over the first K-wire 28 by inserting the free end of the K-wire 28 into the sizing guide aperture 34, and bringing the sizing guide 30 toward the metatarsal 22 to a position whereby the sizing guide 30 is adjacent the metatarsal in sufficiently close proximity to the metatarsal such that the surgeon can properly gauge the size indicators 35 relative to the metatarsal. The trajectory of the first K-wire 28 guides the sizing guide 30 toward the metatarsal 22 such that the sizing guide aperture 34 is brought to a position aligned with the desired position 27 along the central axis of the first K-wire 28.

When the sizing guide 30 is positioned adjacent the metatarsal 22, the surgeon can determine the size of the permanent implant. Each size indicator 35 is spaced from the sizing guide aperture 34 a respective different distance along the length of the sizing guide 30 (and thus along the length of the metatarsal 22). A kit can contain a plurality of permanent implants that correspond to different ones of the size indicators 35. Therefore, when the sizing guide 30 is positioned adjacent the metatarsal 22, the surgeon can identify the size indicator 35 best matches the length of the proximal portion metatarsal 22. The surgeon can then select the permanent implant corresponding to the identified size indicator 35. In one example, the sizing guide contains two size indicators 35 that include written or graphical indicia such as "S" or "L" corresponding to "small" and "large" implant sizes, respectively. It should be appreciated that the size indicators 35 can include any suitable graphical indicia as desired, including distances that correlate to a corresponding permanent implant length or size. Once the permanent implant has been sized, the sizing guide 30 can be removed from the foot 20 by sliding the sizing guide 30 along the first K-wire 28 in a removal direction away from the foot 20 until the sizing guide 30 is removed from the first K-wire. The first K-wire 28 can remain inserted in the metatarsal 22 at the desired position 27 as shown in FIG. 4A.

Figure 5A:
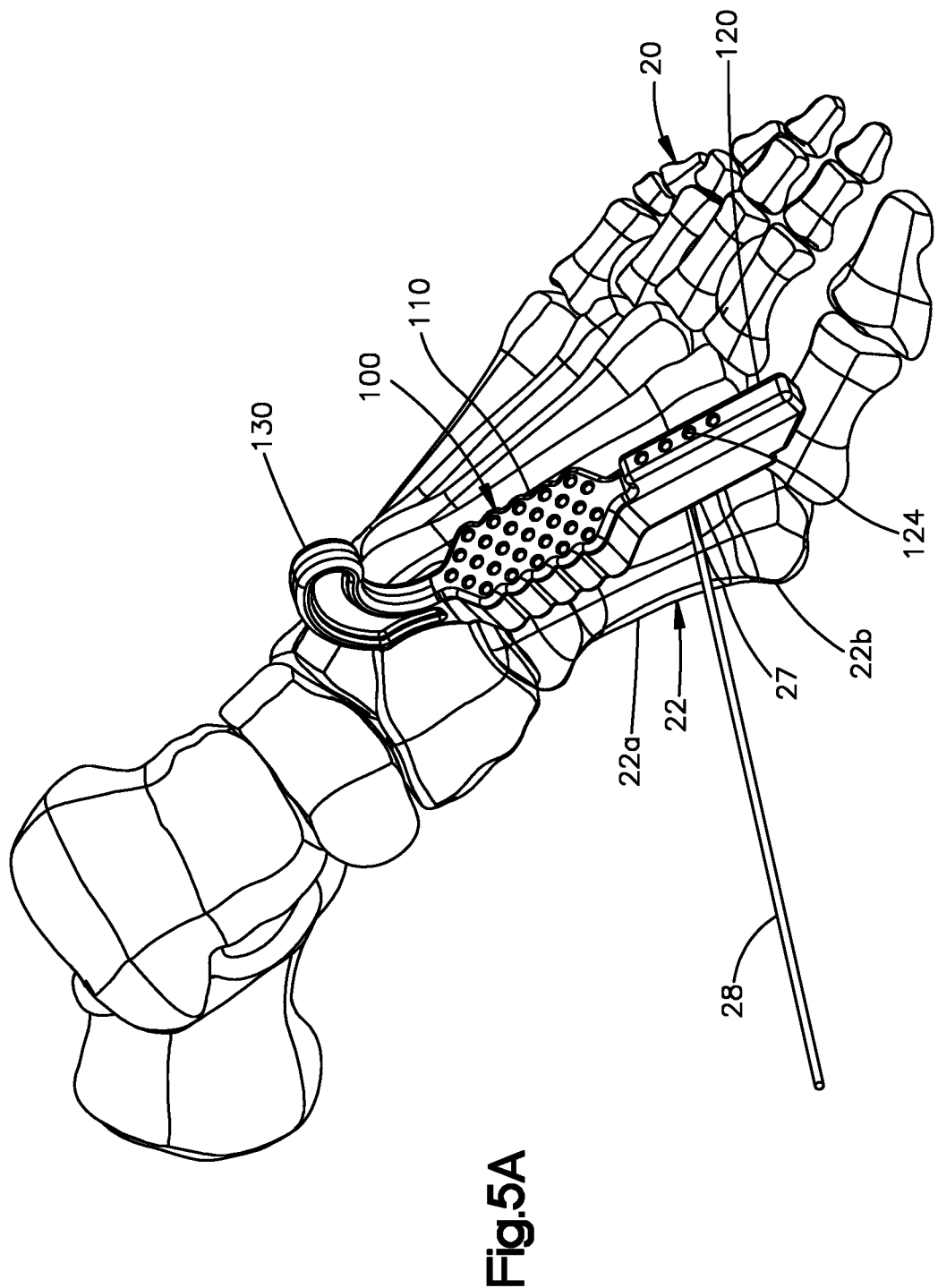
FIG. 5A is a perspective view of the capital fragment guide of FIG. 1 aligned with a distal portion of the first metatarsal of the patient's foot of FIG. 4B, wherein the distal portion is earmarked to define a capital fragment of the first metatarsal.
Figure 5B:
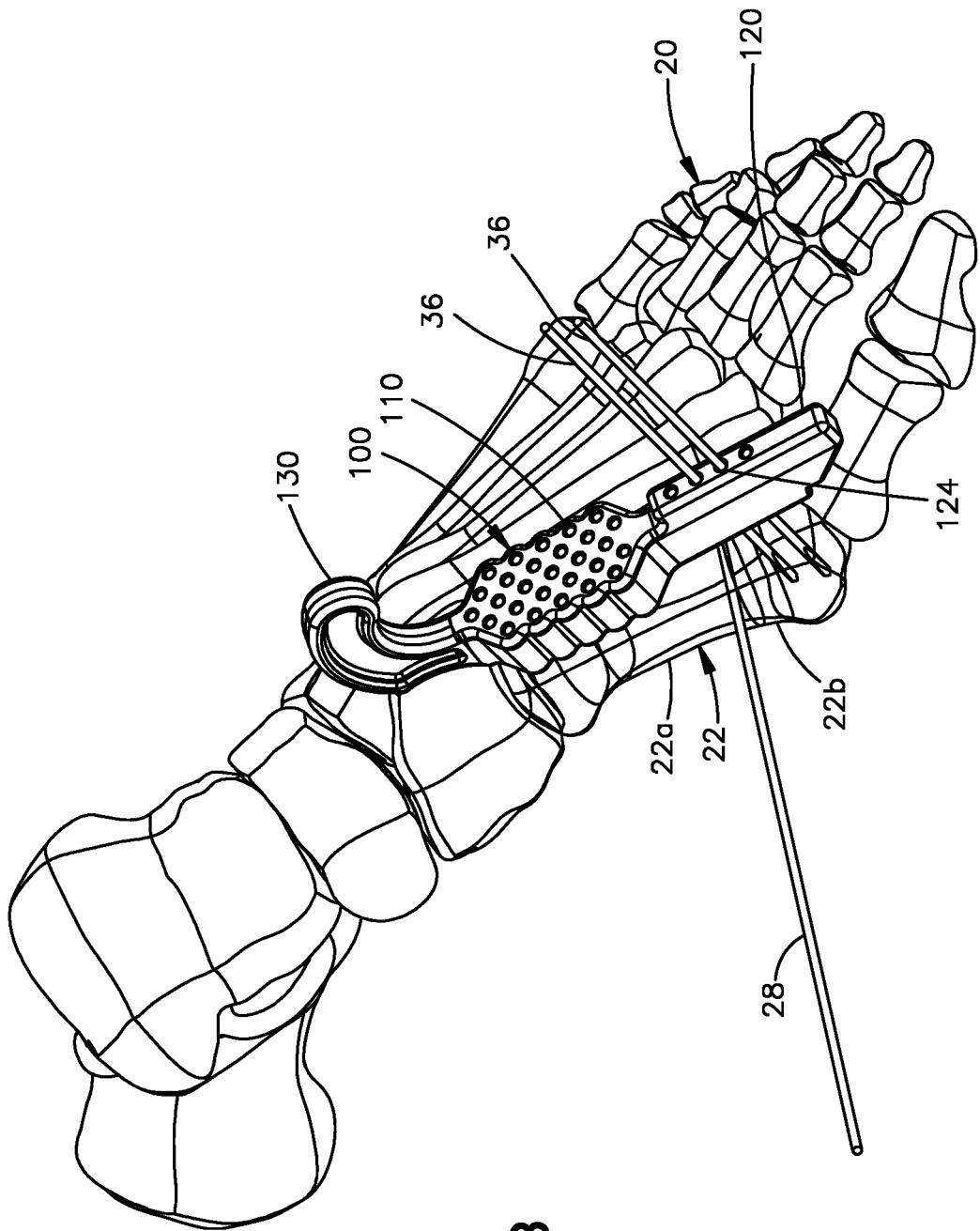
FIG. 5B is a perspective view of the patient's foot of FIG. 5A, showing two K-wires driven into the distal portion of the first metatarsal through alignment apertures of the capital fragment guide.

Referring now to FIGS. 5A-5B, the surgical system can further include one or more temporary fixation devices such as a pair of temporary fixation devices that can be configured as K-wires 36. The K-wires can be inserted into the distal portion 22b of the metatarsal 22 that has been earmarked to define the capital fragment when the metatarsal 22 is later cut. That is, the K-wires 36 can be inserted percutaneously into the metatarsal 22 at respective locations that are distal of the first K-wire 28. The respective locations can be spaced from each other in the anatomical proximal-distal direction. Further, the K-wires 36 can be oriented substantially parallel to each other.

In one example, the K-wires 36 are inserted into the distal portion 22b by first bringing the capital fragment guide 100 to a position aligned with the metatarsal 22, such that one or more of the alignment apertures 124 are aligned with the distal portion 22b of the metatarsal 22 along a trajectory as defined by the central axes of the alignment apertures 124. The capital fragment guide 100 can be disposed external of the incision, and thus external of the patient's body that contains the metatarsal 22. The alignment apertures 124 can have a diameter that is substantially equal to the diameter of the K-wires 36, such that the K-wires 36 are translatable only along the central axes 126 of the alignment apertures 124 as they travel through the alignment apertures 124.

The first K-wires 36 can be driven through respective select alignment apertures 124 of the plurality of alignment apertures 124 to the metatarsal 22 in respective insertion directions, and subsequently rotated so as to purchase the K-wire 36 with the metatarsal 22 as the K-wires 36 travel in the insertion direction into the distal portion 22b of the metatarsal 22. In one example, the K-wires 36 and other K-wires disclosed herein have smooth surfaces that purchase with the underlying bone. In other examples, the K-wires can have threaded surfaces that threadedly purchase with the underlying bone by rotating the K-wire as the K-wire is driven into the underlying bone. The K-wires 36 can be driven through those alignment apertures 124 that are aligned with reliable bone for purchase with the K-wires 36. When the K-wires 36 have been driven through the respective alignment apertures 124 and into the distal portion 22b of the metatarsal, the body portion 110 can be aligned with the proximal portion 22a of the metatarsal 22. Because the K-wires 36 are inserted into the distal portion 22b of the metatarsal 22, the K-wires 36 can be referred to as distal K-wires or distal temporary fixation members. While any number of K-wires 36, such as at least one, can be inserted into the distal portion 22, it is appreciated that at least a pair of K-wires 36 can give the capital fragment guide 100 better control over the positional manipulation of the capital fragment 22c as is described in more detail below (see FIGS. 12A-12B). Further, the at least one K-wire 36 allows the surgeon to easily locate and identify the capital fragment 22c in subsequent surgical steps, which can be particularly advantageous in a minimally invasive surgery having a small incision.

Figure 6:
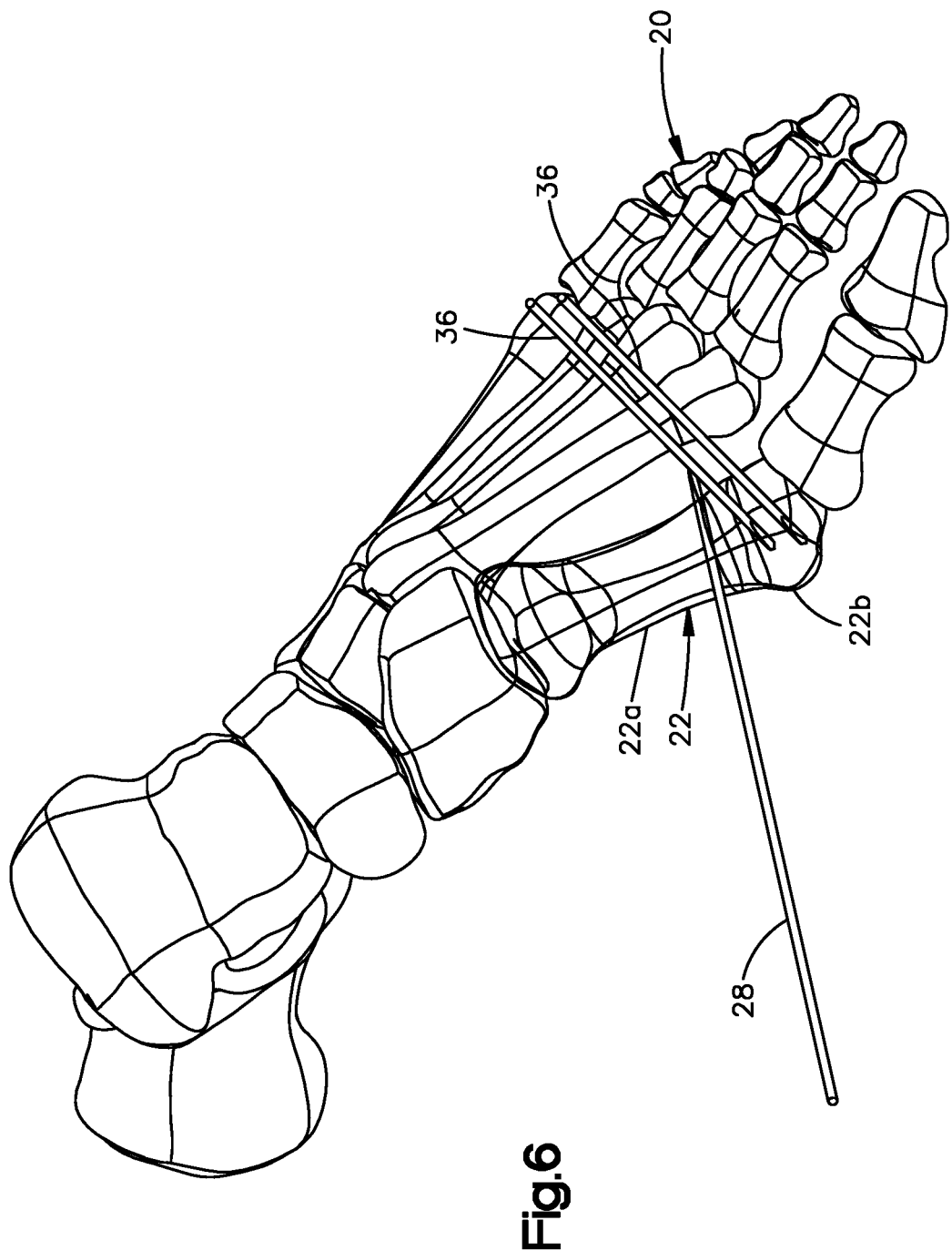
FIG. 6 is a perspective view of the patient's foot of FIG. 5B, showing the capital fragment guide removed while the two k-wires remain inserted in the distal portion of the first metatarsal.
Figure 7A:
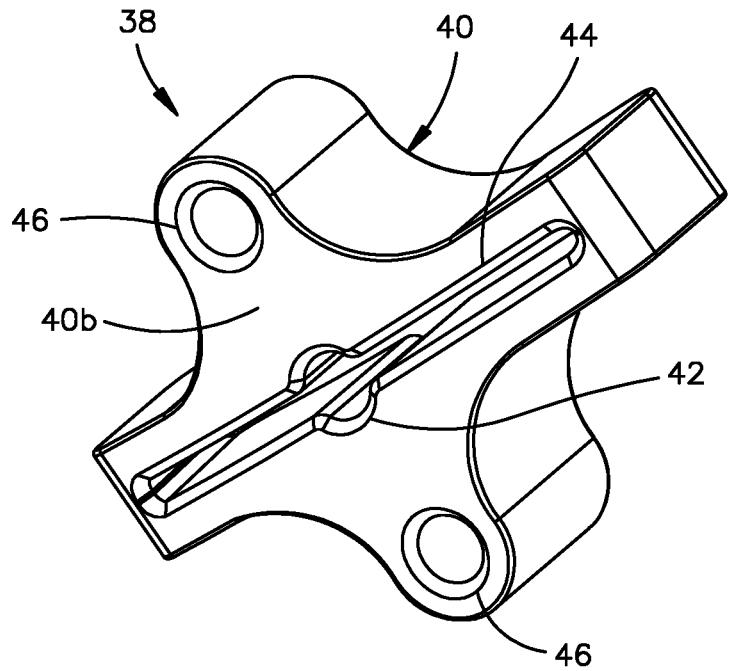
FIG. 7A is a perspective view of a cut guide that is configured to receive a cutting instrument used to cut or resect the first metatarsal so as to separate the distal portion of the first metatarsal, thereby defining a capital fragment of the first metatarsal that is separate from the proximal portion of the first metatarsal.
Figure 7B:
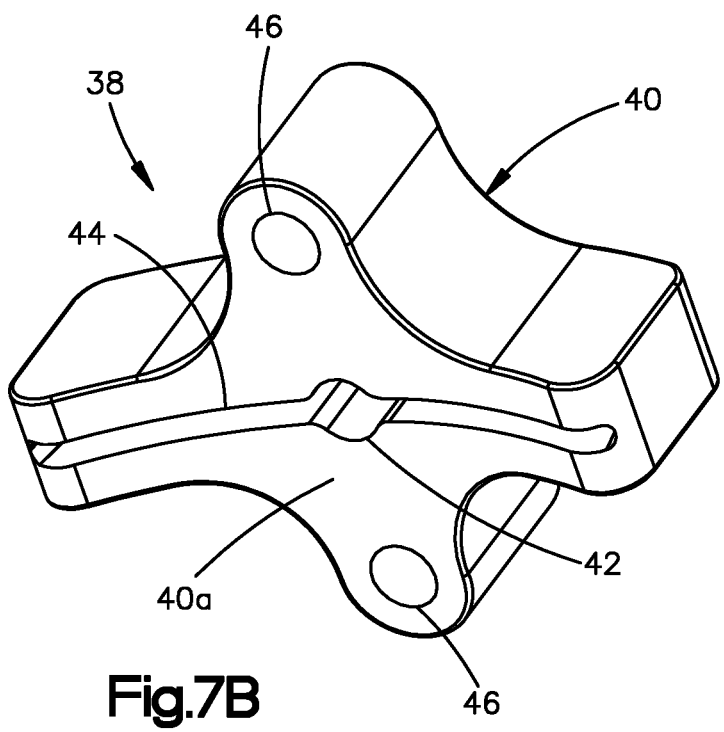
FIG. 7B is another perspective view of the cut guide of FIG. 7A.

Referring now also to FIG. 6, once the K-wires 36 have been driven into the distal portion 22b of the metatarsal 22, the capital fragment guide 100 can be removed by sliding the capital fragment guide 100 along the K-wires 36 in a removal direction that is opposite the insertion direction of the K-wires 36. The K-wires 36 remain inserted in the distal portion 22b of the metatarsal 22. It is appreciated that both the insertion direction and the removal direction can be defined by the central axes 126 of the alignment apertures 124. As will be appreciated from the description below, because the K-wires 36 were driven through the alignment apertures 124, the capital fragment guide 100 can later be positioned over the metatarsal 22 such that the K-wires 36 are again received by the alignment apertures 124.

Referring now to FIGS. 7A-8B, the surgical system can further include a cut guide 38 that is configured to guide a cutting instrument to cut the metatarsal along a desired cut plane. The cut guide 38 can include a cut guide body 40 that defines an inner bone-facing surface 40a and an outer surface 40b opposite the bone-facing surface 40a. The cut guide can include a first or central aperture 42 that extends through the cut guide body 40 from the outer surface 40b to the inner surface 40a along a central axis of the first aperture 42. The first aperture 42 is sized and configured to receive the first K-wire 28. The first aperture 42 can have a diameter substantially equal to that of the first K-wire 28. Accordingly, translation of the first K-wire 28 in the first aperture 42 can occur relative to the cute guide 38 only along the central axis of the first aperture 42.

The cut guide 38 can further include a cutting slot 44 that extends through the cut guide body 40 from the outer surface 40b to the inner surface 40a. The cutting slot 44 can be positioned at a known position with respect to the first aperture 42. Thus, when the first aperture 42 receives the first K-wire 28, the cutting slot 44 can be aligned with the metatarsal at a location that is determined to be resected by a cutting instrument. Thus, the location to be resected can include the desired position 27 of the first K-wire 28 (see FIGS. 4A-4B). The cutting slot 44 can define a length that is measured along a direction that extends along either or both of the inner surface 40a and the outer surface 40b. The cutting slot 44 can define a width that is perpendicular to the length and is less than the length. In one example, an inner portion of the first aperture 42 can be defined by the cutting slot 44, while an outer portion of the first aperture 42 extends beyond the width of the cutting slot 44. In particular, the diameter of the first aperture 42 can be sized greater than the width of the cutting slot 44. As a result, when the first K-wire 28 extends through the first aperture 42, the first K-wire is prevented from translatable or angulating along the length of the cutting slot 44.

In another example, the first aperture 42 can be spaced from the cutting slot 44 by a known distance. Thus, in this example, the desired position 27 of the first K-wire 28 (see FIGS. 4A-4B) can be spaced from the cutting slot by the known distance. Accordingly, when the first K-wire 28 is received by the first aperture 42 of the cut guide 38 that is spaced from the cutting slot 44 by the known distance, the cutting slot 44 can be aligned with the cut plane of the metatarsal that is to be severed. It should be appreciated that the desired position of the first K-wire and the cut plane of the metatarsal can be earmarked as part of preplanning prior to the surgical procedure, or can be identified by the surgeon in real time during the surgical procedure.

The cut guide 38 can further include at least one mounting aperture 46 that extends through the cut guide body 40 from the outer surface 40b to the inner surface 40a. It is recognized that the cut guide 38 is positionally fixed on the metatarsal 22 when the cut guide 38 is secured to the metatarsal at two different fixation points (see FIG. 8B). One of the fixation points can be defined by a temporary mounting fixation device such as a mounting K-wire 48 that is driven through the mounting aperture 46 and into the metatarsal 22. When the first aperture 42 is spaced from the cutting slot 44, another one of the fixation locations can be defined by the first K-wire 28. Thus, in some examples, the cut guide 38 can include only a single mounting aperture 46.

When the first aperture 42 is coincident with the cutting slot 44, the first K-wire 28 is removed prior to cutting the metatarsal 22 through the cutting slot 44. Therefore, the cut guide 38 can include a pair of mounting apertures 46 that are spaced from each other and receive respective mounting K-wires 48 to ensure that the cut guide 38 is positionally fixed with respect to movement along the metatarsal 22. In one example, the cutting slot 44 can be disposed between the mounting apertures 46. The mounting apertures 46 can have a diameter that is sized substantially equal to the diameters of the temporary mounting fixation devices that can be configured as mounting K-wires 48. Thus, when the mounting K-wires 48 are driven through the mounting apertures 46, respectively, and into the metatarsal 22, the cut guide 38 is prevented from moving along the metatarsal 22. An example of the cut guide 48 is shown and described with respect to FIGS. 4-8 and 14A-E of U.S. Pat. Pub. No. 2021/0038260, the entirety of which is incorporated by reference. The surgical system can further include the mounting K-wires 48.

With continuing reference to FIGS. 7A-8B, during operation the cut guide 38 is inserted through the incision and placed over the metatarsal 22 such that the first aperture 42 receives the first K-wire 28. Next, the cut guide 38 can be rotated about an axis of rotation that can be defined by the first K-wire 28, to align the cutting slot 44 with the cut plane that is to be cut so as to separate the distal portion 22b from the proximal portion 22a of the metatarsal 22. When the first aperture 42 is partially defined by the cutting slot 44, the mounting K-wires 48 can be driven through the mounting apertures 46 and into the metatarsal to positionally fix the cut guide 38 whereby the cutting slot 44 is aligned with the desired cut plane. Because the mounting apertures 46 can be disposed on opposite sides of the cutting slot 44, it should be appreciated that a proximal one of the mounting K-wires 48 is driven through one of the mounting apertures 46 and into the proximal metatarsal portion 22a, and a distal one of the mounting K-wires 48 is driven into another one of the mounting apertures 46 and into the distal metatarsal portion 22b.

Figure 8A:
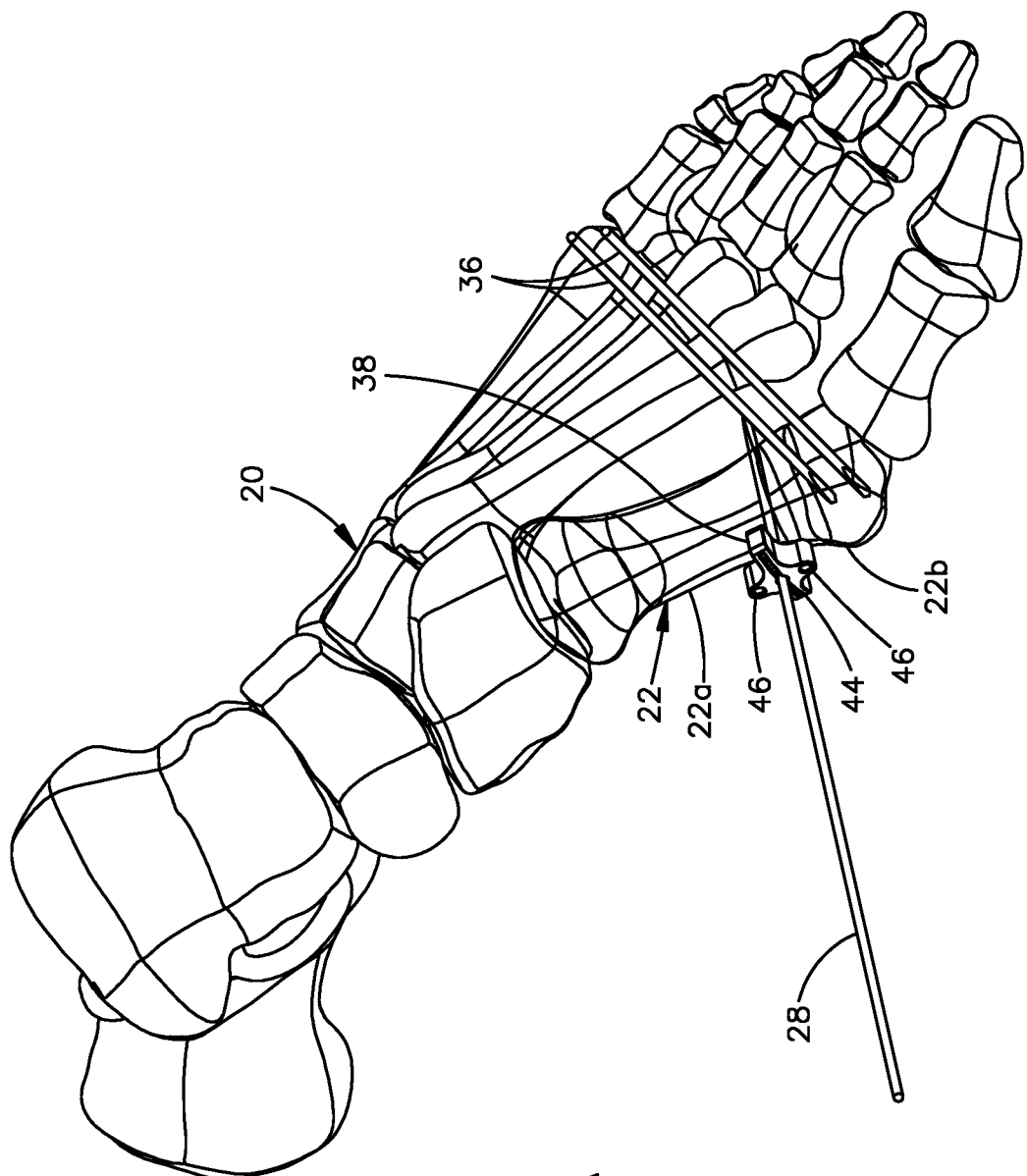
FIG. 8A is a perspective view of the patient's foot of FIG. 6, showing the cut guide of FIG. 7A guided along the first K-wire of FIG. 4B to an interface between the proximal portion of the first metatarsal and the distal portion of the first metatarsal.
Figure 8B:
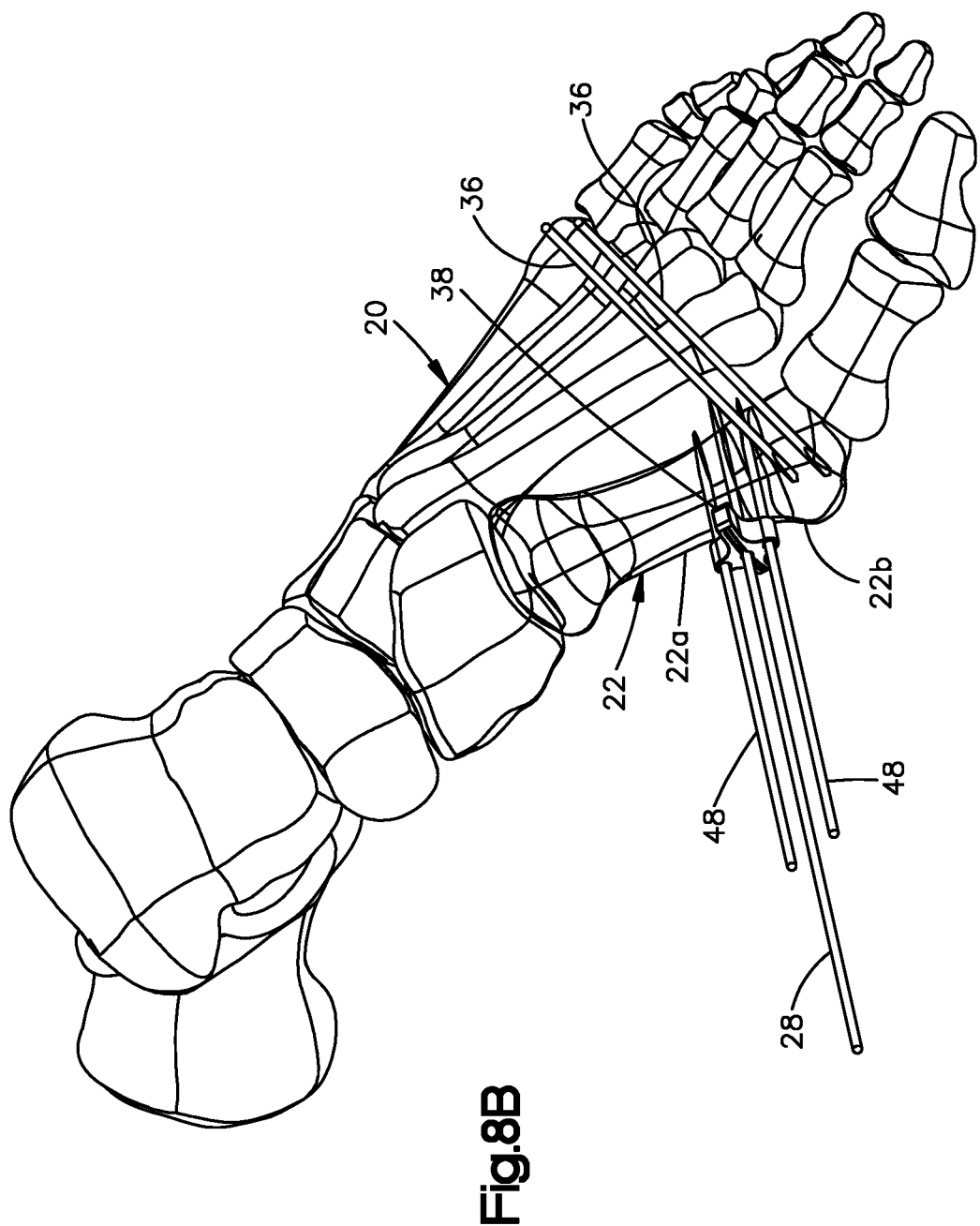
FIG. 8B is a perspective view of the patient's foot of FIG. 8A, showing the cut guide aligned with the first metatarsal in position to guide a cutting instrument that cuts the first metatarsal.
Figure 9:
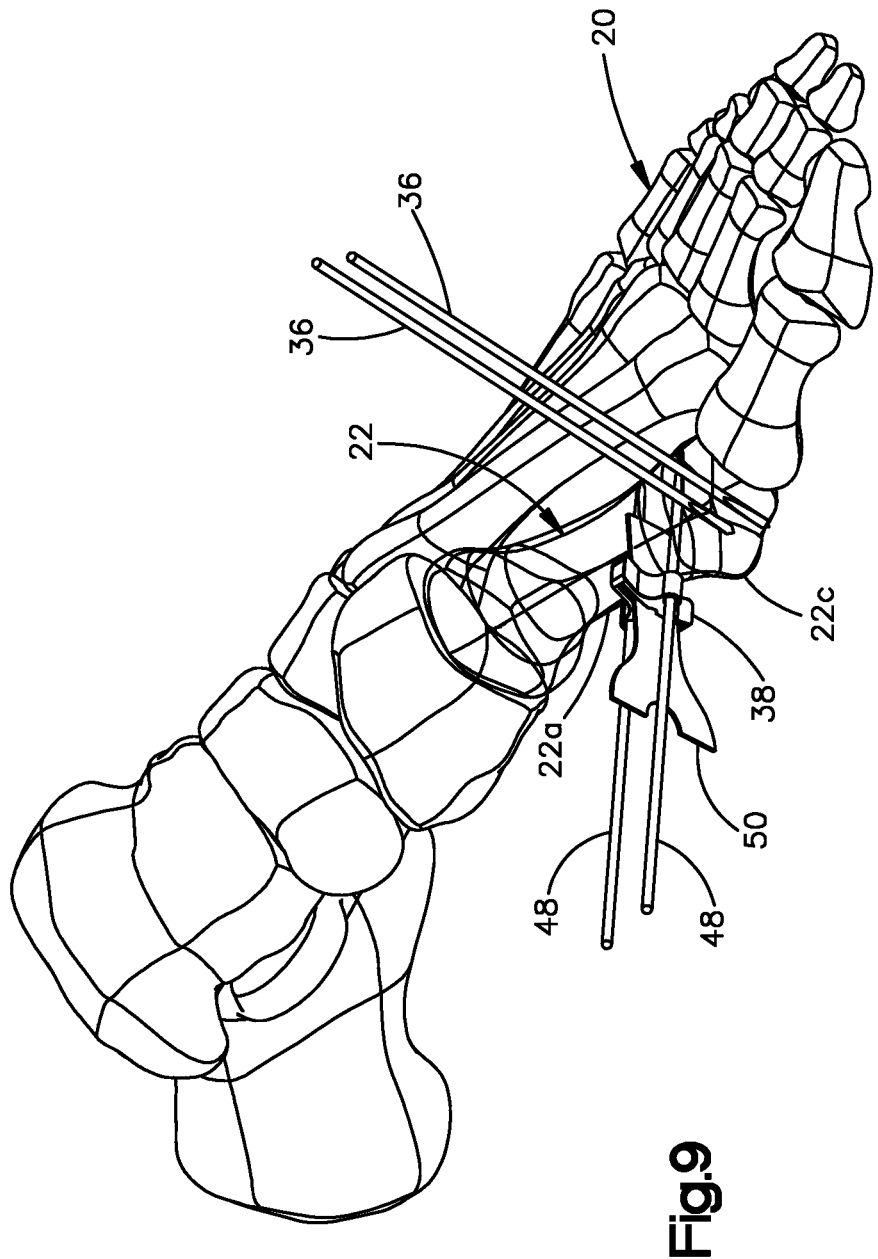
FIG. 9 is a perspective view of the patient's foot of FIG. 8B, showing a cutting instrument inserted into cut guide and guided by the cut guide to cut/resect the first metatarsal so as to define the capital fragment that is separated from the proximal portion of the first metatarsal.

Referring now to FIGS. 8B-9, the first K-wire 28 can be then removed from the metatarsal 22 so as to expose an entirety of the cutting slot 44. Because the mounting K-wires 48 provide two points of fixation of the cut guide 38 to the metatarsal 22, the cut guide 38 is unable to translate or angulate along the metatarsal. Thus, the cutting slot 44 remains aligned with the earmarked cut plane. In other examples whereby the first aperture 42 is spaced from the cutting slot 44, the first K-wire 28 can remain inserted in the first aperture during the cutting procedure, as the underlying metatarsal 22, and only a single mounting K-wire 48 and the first K-wire 28 can provide the two points of fixation to stabilize the cut guide 38.

Next, referring also to FIG. 9, a cutting instrument 50 can sever the metatarsal 22, thereby dividing the metatarsal into the proximal portion 22a and the capital fragment 22c. The capital fragment 22c was previously defined by the distal portion of the metatarsal 22. The cutting instrument 50 can be configured as a saw, reamer, burr or any suitable alternative instrument. The surgical system can further include the mounting cutting instrument 50. The capital fragment 22c is defined by the distal portion 22b that has been resected and separated from the proximal portion 22a. The cutting instrument 50 can be inserted into the cutting slot 44 and into the metatarsal 22 along the cut plane that has been earmarked. Movement of the cutting instrument 50 along the cut plane through the metatarsal 22 separates the distal portion 22b of the metatarsal 22 from the proximal portion 22a, such that the distal portion 22b defines the capital fragment 22c. The cutting instrument 50 can then be removed from the cut guide 38, the cut guide 38 and mounting K-wires 48 can be removed from the metatarsal 22. The cut guide 38 can be removed from the mounting K-wires 48 in a direction opposite the insertion direction, and the mounting K-wires 48 can then be removed from the metatarsal 22. Alternatively, the mounting K-wires 48 can be removed from the metatarsal 22, and then the assembly of the K-wires 48 and the cut guide 38 can be removed. One more of the distal K-wires 36 can be gripped to stabilize the capital fragment 22c while removing the distal mounting K-wire 48 from the capital fragment 22c as desired. While a procedure has been described for separating a distal portion of the metatarsal from a proximal portion of the metatarsal and manipulating the distal portion of the metatarsal with respect to the proximal portion of the metatarsal so as to align the distal portion with the proximal portion, it should be appreciated that the procedure can apply to any bone as desired so as to separate a second portion of a bone from a first portion of the bone such that the second portion defines a separated second portion, and to manipulate the separated second portion of the bone with respect to the first portion of the bone so as to align the separated second portion with the first portion.

Figure 10A:
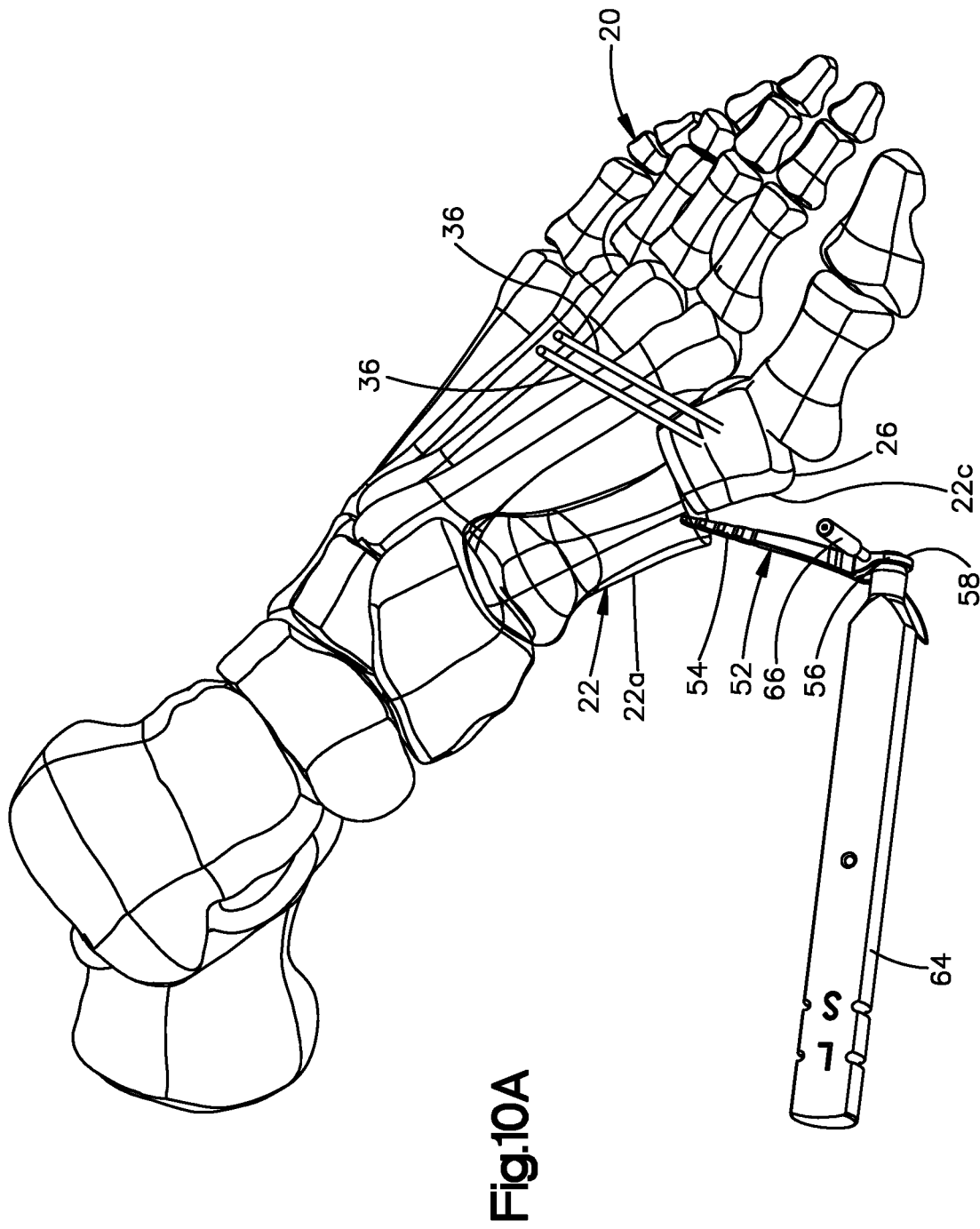
FIG. 10A is a perspective view of the patient's foot of FIG. 9, showing the cut/resected first metatarsal, and further showing an implant coupled to an inserter and aligned for insertion into a distal facing end of the proximal portion of the metatarsal that has been exposed by shifting of the capital fragment to an offset position relative to proximal portion.
Figure 10B:
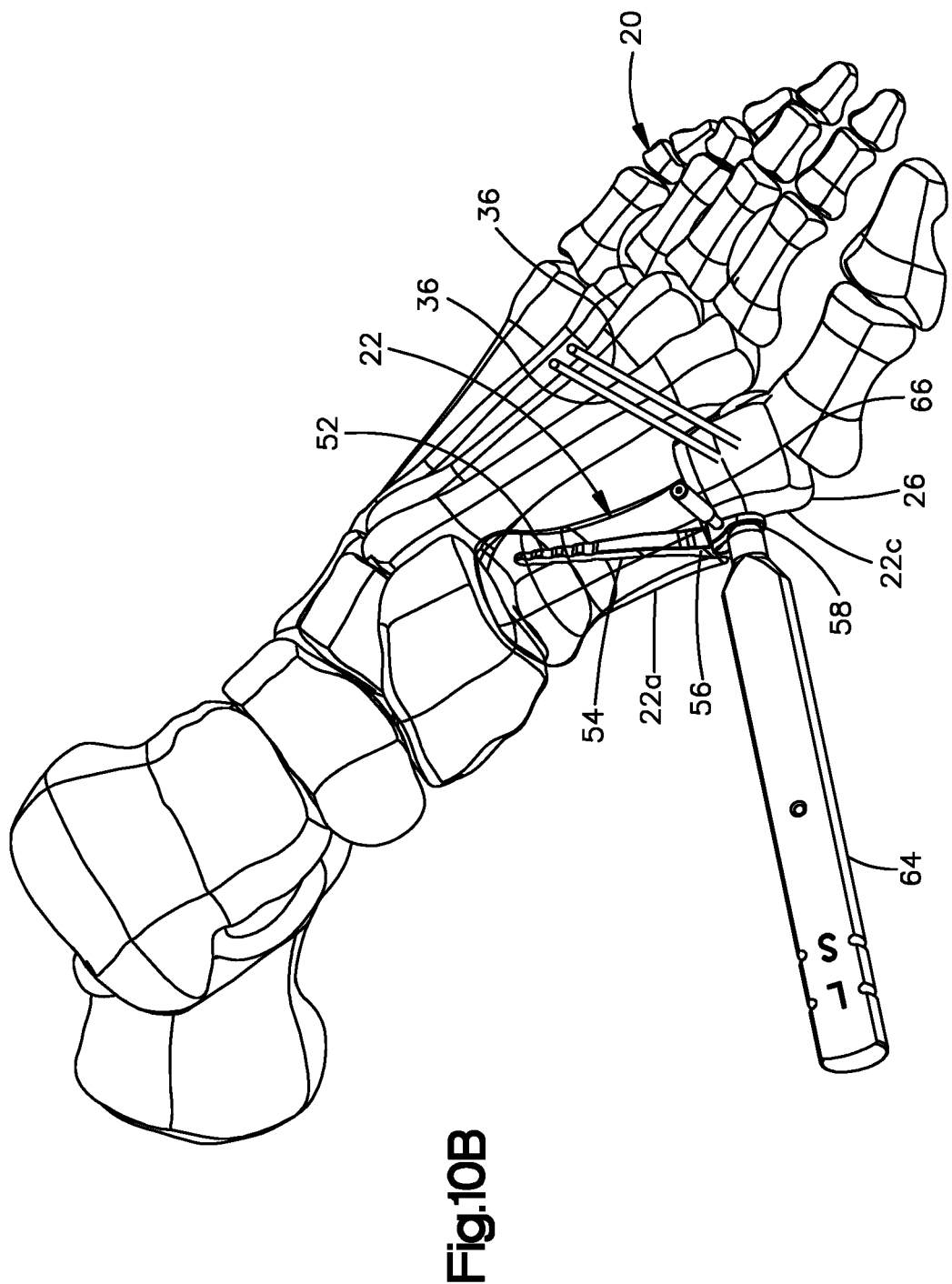
FIG. 10B is a perspective view of the patient's foot of FIG. 10A, showing the implant seated in the proximal portion of the first metatarsal by the inserter.
Figure 10C:
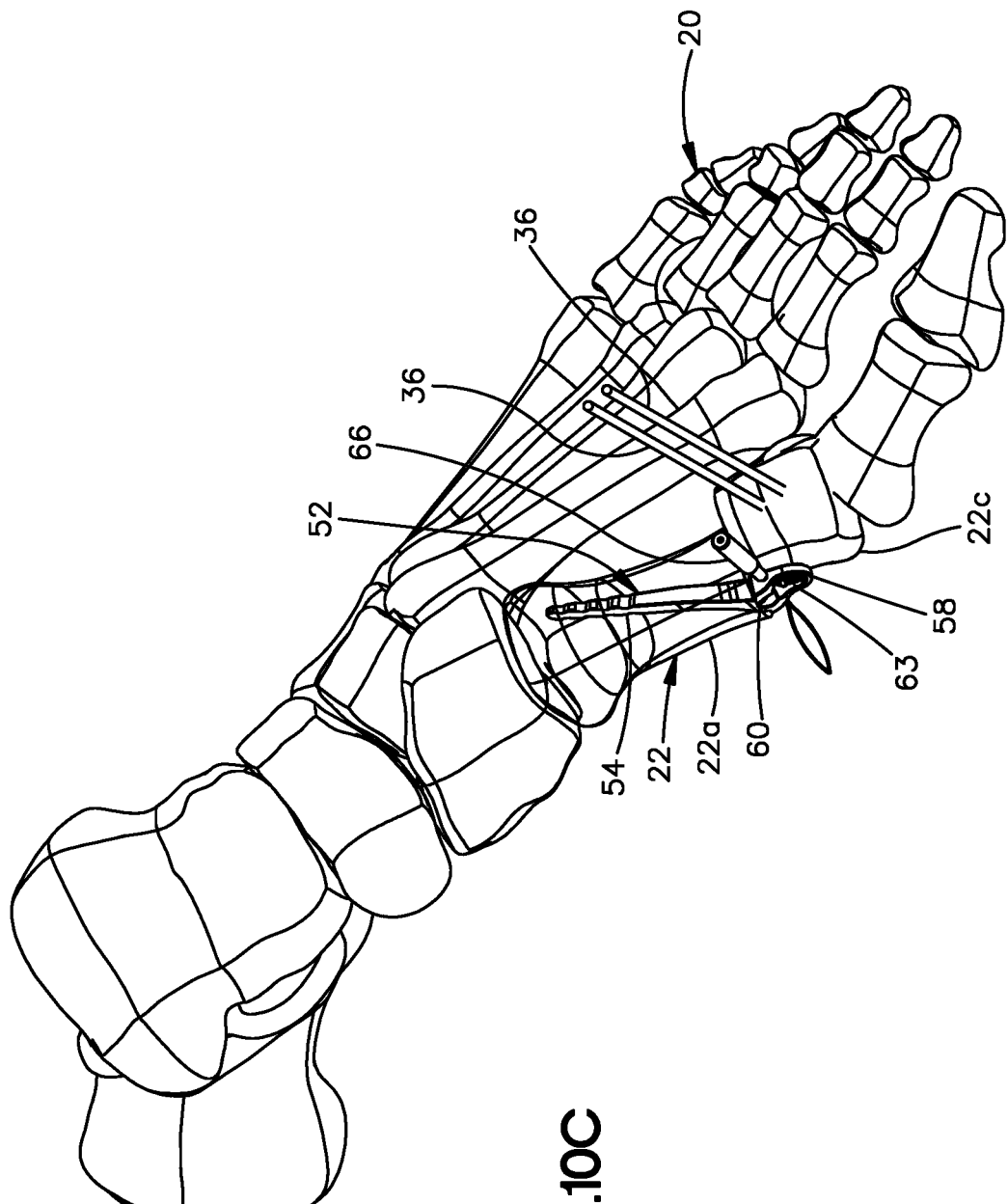
FIG. 10C is a perspective view of the patient's foot of FIG. 10B, showing the implant fully seated in the proximal portion of the first metatarsal, and the inserter removed.

Referring now to FIGS. 10A-10C, the surgical system can further include an implant 52 that is configured to fix the proximal portion 22a of the metatarsal 22 to the capital fragment 22c after the capital fragment 22c has been repositioned to correct the bunion 26. The implant 52 can include a nail portion 54, a neck 56 that extends from the nail portion 54, and a head 58 that extends from the neck 56. The nail portion 54, the neck 56, and the head 58 can define a single unitary monolithic body. The nail portion 54 is sized and configured to be inserted into the medullary canal of the proximal portion 22a of the metatarsal 22 through a distal end of the medullary canal. The head 58 can extend along the capital fragment 22c, and can define a distal fixation aperture 62 that is configured to receive a bone fixation element to secure the implant 52 to the distal portion 22b. The head 58 can also be configured to removably couple to an inserter 64. The neck 56 can extend from the nail portion 54 to the head 58. The neck 56 can further define a proximal fixation aperture 60 that is configured to receive a bone fixation element to secure the implant 52 to the proximal portion 22a. The proximal fixation aperture 60 can extend through the neck 56 of the implant 52. The distal fixation aperture 62 can extend through the head 58 of the implant 52. As will be described in more detail below, the implant 52 can be fixed to the proximal portion 22a, the capital fragment 22c can be positionally manipulated to a desired position, and the implant 52 can then be fixed to the capital fragment 22c to secure the distal portion in the desired position.

Referring to FIG. 10A in particular, the implant 52 can be removably coupled to an inserter 64 that can be included in the surgical system. The inserter 64 can be defined by the same instrument that defines the guide 30 (see FIG. 4A) in some examples. Alternatively, the inserted 64 can be defined by a separate instrument as desired. The inserter 64 can be manipulated so that the nail portion 54 is aligned with the distal end of the medullary canal of the proximal portion 22a of the metatarsal 22. The capital fragment 22c can be moved or shifted to an offset position with respect to the proximal portion 22a in order to expose the distal end of the medullary canal, thereby providing access for the nail portion 54 to be inserted through the distal end and into the medullary canal. A manual force can be applied to the capital fragment 22c that causes the capital fragment 22c to move shift laterally with respect to the proximal portion 22a to the offset position.

As illustrated in FIG. 10B, the inserter 64 can drive the nail portion 54 of the implant 52 into the medullary canal until the nail portion 54 is fully seated in the medullary canal. The inserter 64 can then be removed as illustrated in FIG. 10C. The implant 52 can be fully seated in the medullary canal such that the proximal fixation aperture 60 is aligned with the proximal portion 22a of the metatarsal 22, and the distal fixation aperture 62 is aligned with the distal portion 22b of the metatarsal 22. In particular, the implant 52 can be positioned such that the surgeon has easy access to the apertures 60 and 62 for the insertion of respective bone fixation element therethrough. Further, the apertures 60 and 62 can be positioned where the anatomy can best accommodate the bone fixation elements. For instance, the apertures 60 and 62 can be positioned generally in alignment with the medial aspect of the metatarsal 22. The implant 52 can include an outwardly extending handle 66 that can be grasped by the surgeon to assist in positioning the implant 52 as desired.

Figure 11A:
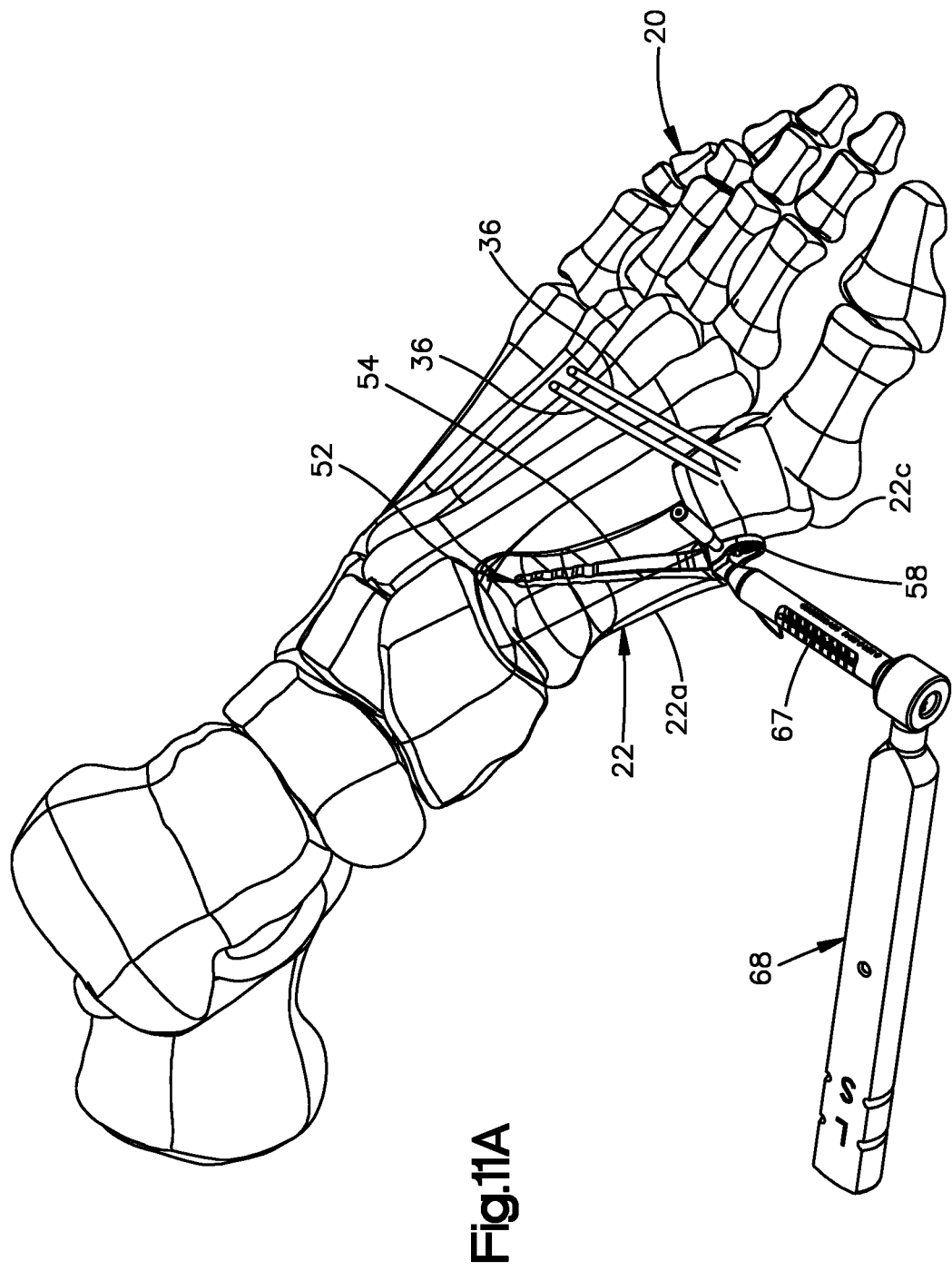
FIG. 11A is a perspective view of the patient's foot of FIG. 10C, showing a drill guide positioned to guide a drill that creates a proximal bone fastener hole in the proximal portion of the first metatarsal.
Figure 11B:
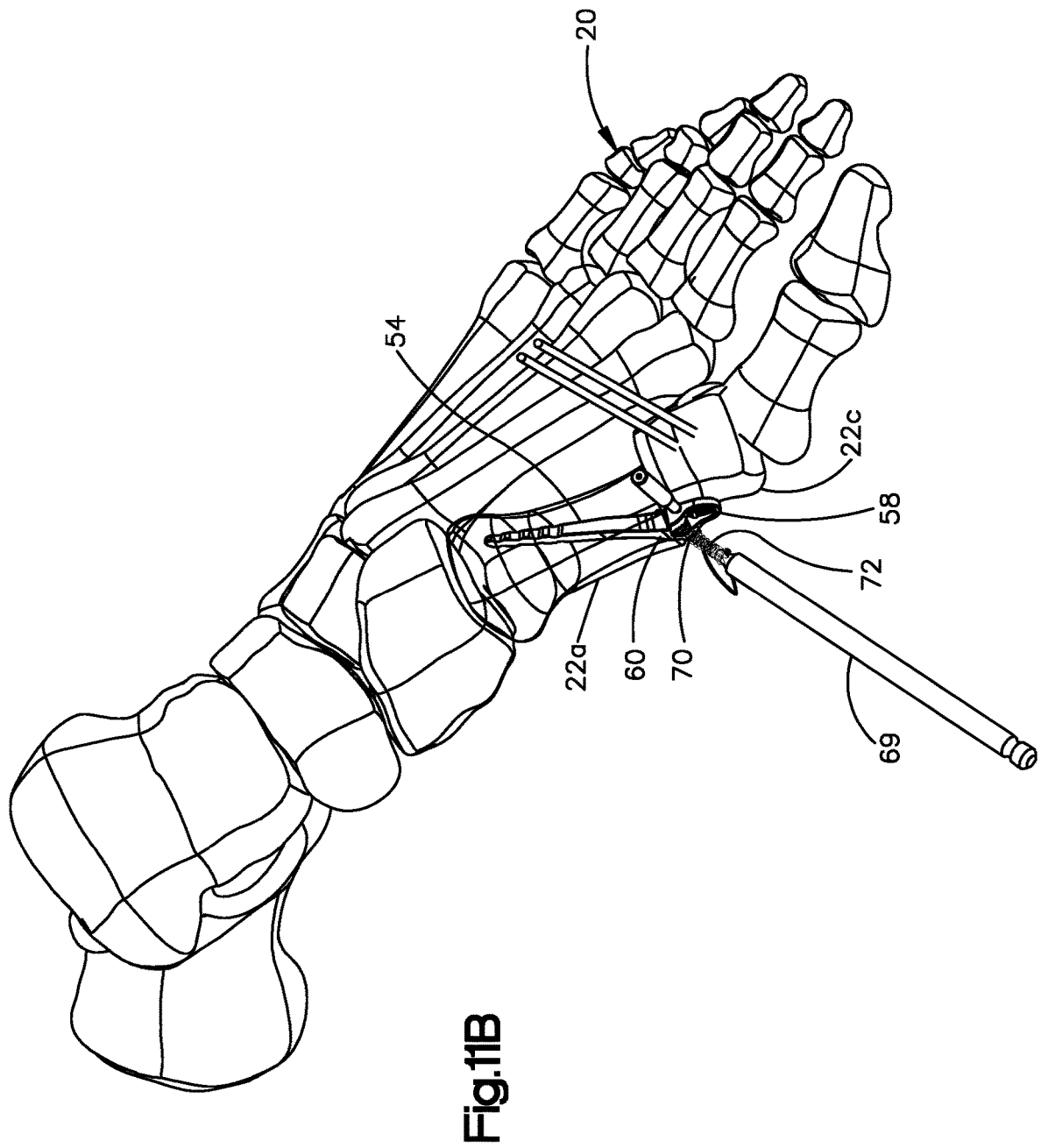
FIG. 11B is a perspective view of the patient's foot of FIG. 11A, showing the proximal bone fastener being driven through the implant and into the bone fastener hole of the proximal portion of the first metatarsal.
Figure 11C:
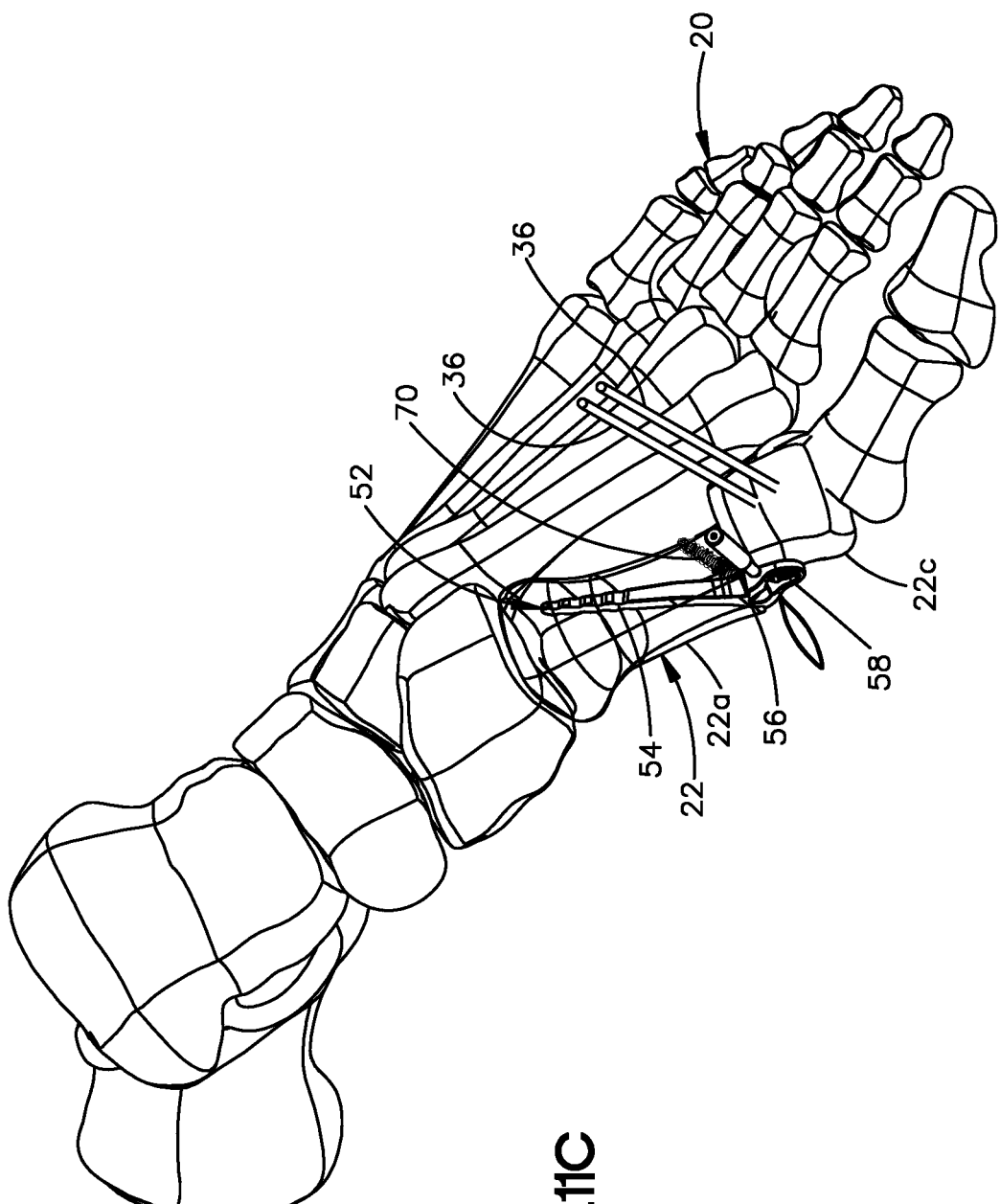
FIG. 11C is a perspective view of the patient's foot of FIG. 11B, showing the implant secured to the proximal portion of the first metatarsal.

Referring now to FIGS. 11A-11C, once the implant 52 has been inserted into the proximal portion 22a of the metatarsal 22 in its desired position, the implant 52 can be permanently fixed to the proximal portion 22a. The term "permanently" is used to indicate that the fixation remains after completion of the surgical procedure. During operation, as shown in FIG. 11A, a handle 68 can support a drill guide 67 that receives a drill that can be driven through the proximal fixation aperture 60 and into the proximal portion 22a of the metatarsal 22 so as to create a hole that will receive a bone fastener. As illustrated in FIG. 11B, driver instrument 69 can drives a proximal bone fastener 70 through the proximal fixation aperture 60 and into the created hole of the proximal portion 22a. In other examples, the proximal bone fastener 70 can be driven into the proximal portion 22a without first preparing the proximal portion 22a with the hole. The handle 68 can be defined by the same instrument that defines the guide 30 (see FIG. 4A) and the inserter 64 (see FIGS. 10A-10B). Alternatively, the handle 68 can be defined by a separate instrument as desired.

The surgical system can include the proximal bone fastener 70. The central axis of the proximal fixation aperture 60 can extend along a trajectory that is oriented laterally and posteriorly. Thus, the proximal bone fixation aperture can be referred to as oblique. The proximal bone fastener 70 can be driven along the central axis of the proximal fixation aperture 60 (e.g., laterally and posteriorly) through the proximal fixation aperture 60 and into the proximal portion 22a. Thus, the proximal bone fastener 70 can likewise be referred to as oblique. In one example, the proximal bone fastener 70 can be configured as a proximal bone screw having a threaded shaft 72 that threadedly purchases with the proximal portion 22a. The bone fastener 70 can include a head (not shown) that becomes seated against the implant 52 in the proximal fixation aperture 60. The head can be unthreaded so as to provide compression against the implant 52 as the proximal bone screw is driven into the proximal portion 22a. In some examples, the head can be threaded so as to threadedly purchase with the implant 52 in the proximal fixation aperture 60. When the bone fastener is seated against the implant and is inserted into the proximal portion 22a, the implant 52 is secured and fixed to the proximal portion 22a with respect to relative movement. Thus, movement of the implant 52 relative to the proximal portion 22a is prevented. The implant 52 is not unattached to the capital fragment 22c, such that the capital fragment 22c is movable with respect to the proximal portion 22a.

Figure 12A:
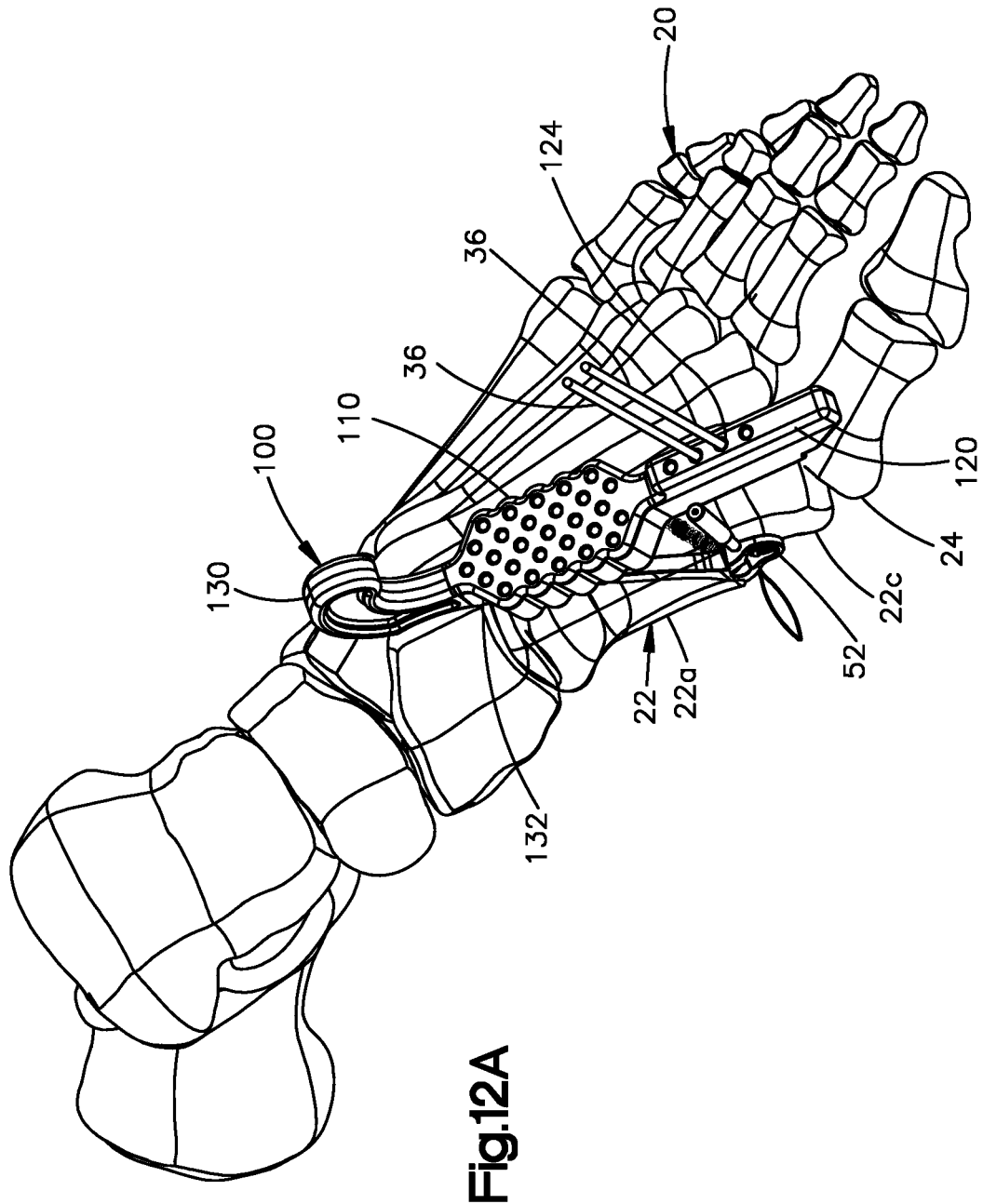
FIG. 12A is a perspective view of the patient's foot of FIG. 11C, the capital fragment guide positioned over the two K-wires shown in FIG. 5B, such that the two K-wires extend through the capital fragment guide.
Figure 12B:
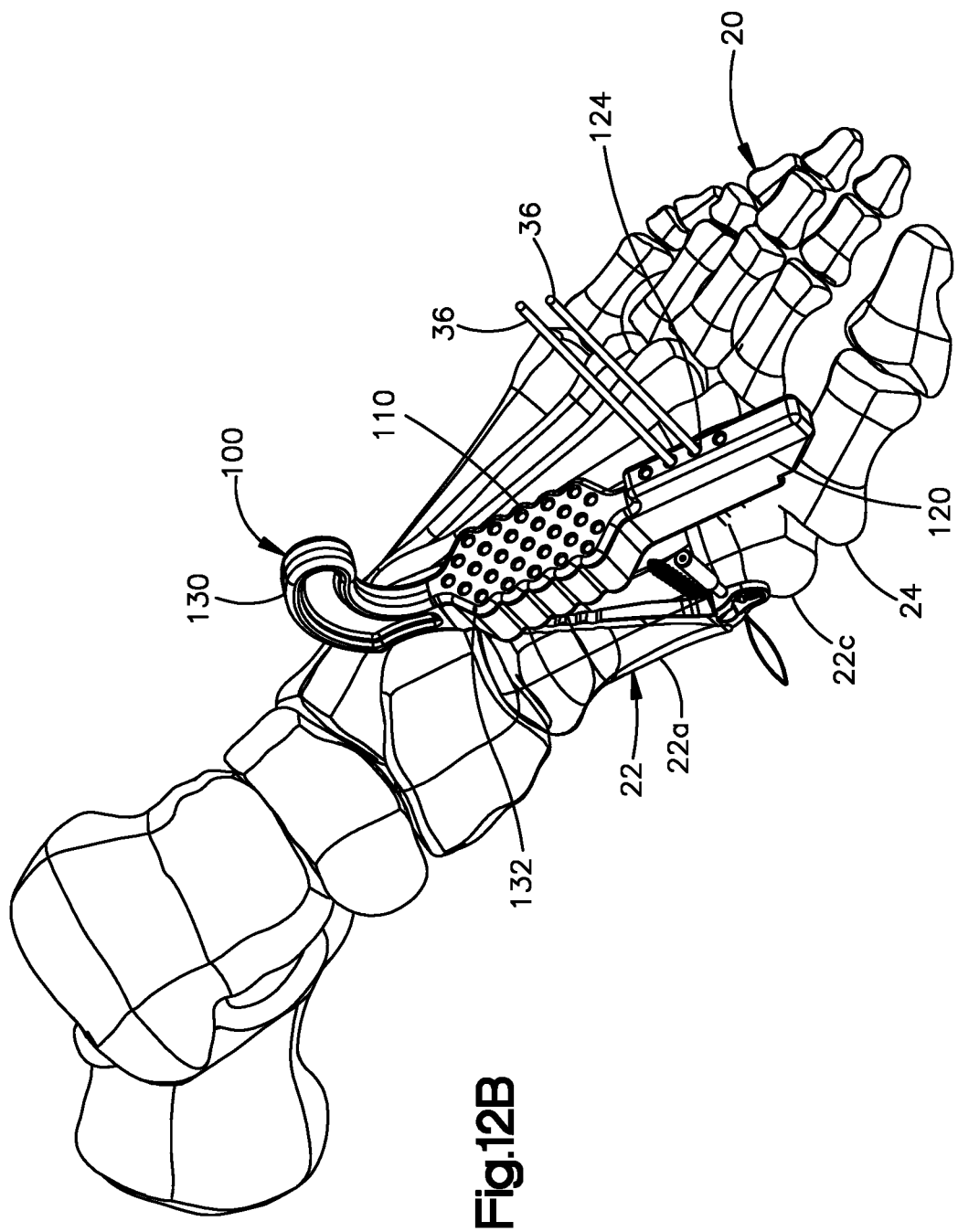
FIG. 12B is a perspective view of the patient's foot of FIG. 12A, showing adjustment of the capital fragment from a misaligned position to a realigned position with respect to the proximal portion using the capital fragment guide.
Figure 12C:
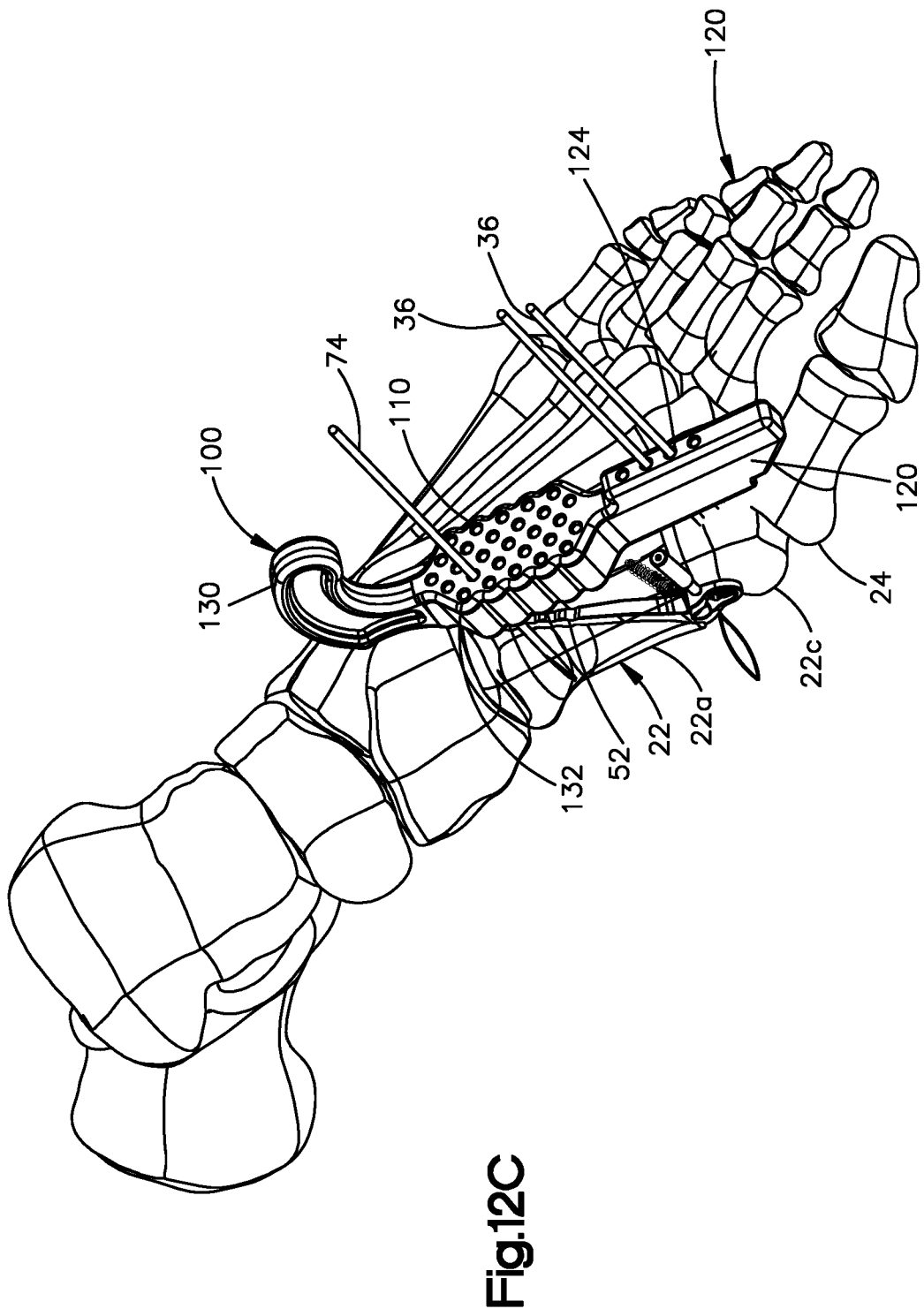
FIG. 12C is a perspective view of the patient's foot of FIG. 12B, showing a third K-wire driven into the proximal portion of the first metatarsal through a guide aperture of the capital fragment guide, such that the capital fragment guide positionally fixes the capital fragment to the proximal portion.

Referring now to FIGS. 12A-12C, the at least one distal K-wire 36 can be moved with respect to the proximal portion 22a so correspondingly move and reposition the capital fragment 22c into alignment with respect to the proximal portion 22a, thereby eliminating the bunion 26 (see FIG. 4). In one example, the capital fragment guide 100 can be temporarily coupled to capital fragment 22c, such that movement of the capital fragment guide 100 with respect to the proximal portion 22a correspondingly moves the capital fragment 22c with respect to the proximal portion 22a. For instance, the capital fragment guide 100 can be recoupled to the distal K-wires 36, which remain temporarily fixed to the capital fragment 22c.

The capital fragment guide 100 can be repositioned over the distal K-wires 36 such that the distal K-wires 36 are again received in respective ones of the alignment apertures 124. In particular, the K-wires 36 can be received in the alignment apertures 124 that the K-wires 36 were previously inserted through when previously fixed to the distal portion 22b as described above with respect to FIGS. 5A-5B. Alternatively, the K-wires 36 can be received by different alignment apertures 124 than the alignment apertures 124 that the K-wires 36 were previously inserted through when being fixed to the distal portion 22b, for instance, when the alignment apertures 124 are all spaced from each other by the same distance. When the K-wires 36 are received in the respective alignment apertures 124, the body portion 110 of the capital fragment guide 100 can be positioned over the proximal portion 32a such that at least one of the body portion apertures 132 is aligned with the proximal portion 32a along its respective central axis. Accordingly, once the capital fragment 22c has been manipulated to a desired translationally and rotationally aligned position with respect to the proximal portion 22a, at least one K-wire can then be inserted through a respective at least one of the body portion apertures 132 and into the proximal fragment 22a to temporarily fix the distal fragment 22c to the proximal fragment 22a.

The K-wires 36 and/or the capital fragment guide 100 allows the surgeon to track and reposition the capital fragment 22c to provide a surgical correction to the bunion or otherwise realign or otherwise align the capital fragment 22c with the proximal portion 22a. In particular, the surgeon can then grasp the handle portion 130, the body portion 110, or other portion of the capital fragment guide 100, and correspondingly translate the capital fragment guide 100, and in particular the alignment portion 120, with respect to the proximal portion 22a medially, laterally, posteriorly, anteriorly, or in any suitable combination thereof Alternatively or additionally, the surgeon can angulate the capital fragment guide 100, and in particular the alignment portion 120, with respect to the proximal portion 22a about an anatomical medial-lateral axis, an anatomical anterior-posterior axis, an anatomical superior-inferior axis, or any axis that is defined by a combination of two or all three of the anatomical axes.

Because the alignment portion 120 is positionally fixed to the capital fragment 22c by the K-wires 36, the translation and/or angulation (referred to as movement or manipulation) of the alignment portion 120 correspondingly translates and/or angulates the K-wires 36, which in turn translates and/or angulates the capital fragment 22c from an initial misaligned position shown in FIG. 12A to an aligned position that is aligned with the proximal portion 22a as shown in FIG. 12B, thereby eliminating the bunion. Because the alignment portion 120 is fixed with respect to the body portion 110 and the handle 130 of the capital fragment guide 100, movement of the capital fragment guide 100 causes movement of the alignment portion 120, which in turn causes movement of the underlying capital fragment 22c. Thus, the capital fragment 22c can be positionally manipulated with respect to the proximal portion 22a to an aligned position whereby the capital fragment 22c is aligned with the proximal portion 22a. In the aligned position, the capital fragment 22c is more aligned with the proximal portion 22a when compared to the alignment of the distal portion with respect to the distal portion 22b prior to separating the distal portion 22b from the proximal portion 22a. During the alignment of the capital fragment 22c, the surgeon can pay particular attention to the adjusted angle of the metatarsal 22 and the proximal phalanx 24. In addition, the surgeon can ensure that at least one of the body portion apertures 132 of the body portion 130 is aligned with the proximal portion 22b of the metatarsal 22. It should be appreciated that the capital fragment is disposed external to the incision and the patient's body as the capital fragment 22c is moved to the aligned position.

In one example, the alignment portion 120 is fixed to the body portion 110 and the handle portion 130 of the capital fragment guide 100, so that movement of the capital fragment guide 100 causes the movement of the alignment portion 120. In other examples, the alignment portion 120 can be movable with respect to the body portion 110, and thus independently manipulated to reposition the capital fragment 22c. For instance, as shown at FIG. 12D, the alignment portion 120 can be attached to the body portion 110 at a joint 143 that allows for movement of the alignment portion 120 relative to the body portion 110 in the manner described herein. Thus, one or more K-wires can temporarily fix the body portion 110 to the proximal portion 22a while the alignment portion 120 is manipulated with respect to the body portion 110.

Advantageously, because the K-wires 36 can be inserted percutaneously into the capital fragment 22c in the manner described above, capital fragment guide 100 can be disposed external of the human body. Thus, the surgical procedure can be performed minimally invasively, with an incision through the dermal and soft tissue layers adjacent the metatarsal only long enough to accommodate insertion of the cut guide 38 (see FIGS. 7A-8B) through the incision onto the metatarsal 22 and insertion of the implant 52 through the incision and into the medullary canal proximal portion 22a and against the capital fragment 22c (see FIGS. 10A-10C). In one example, the incision can be in a range from approximately 5 mm to approximately 30 mm, such as from approximately 10 mm to approximately 20 mm, in length.

Referring now to FIG. 12C, once the capital fragment 22c has been moved to the aligned position, the capital fragment 22c can be positionally fixed to the proximal fragment 22a. In particular, at least one proximal temporary fixation device such as a proximal K-wire 74 can be driven percutaneously through one of the apertures 132 of the body portion 110 and inserted into the underlying proximal portion 22a. It should be appreciated that one or more proximal K-wires 74 can be driven through respective apertures 132 at one or more of the sections 134-136 (see FIG. 2G) of apertures 132 in the body portion 130. The surgical system can include the one or more proximal K-wires 74. The apertures 132 provides the surgeon with positional flexibility for the at least one K-wire 74 to be driven into reliable bone of the proximal portion 22a for purchasing with the at least one K-wire 74 at a position that is does not interfere with the implant 52 and the proximal bone fastener 70. Different sections 134-136 may be better aligned with the proximal portion 22a of the left foot or the right foot, depending on the orientation of the capital fragment guide 100.

Figure 13A:
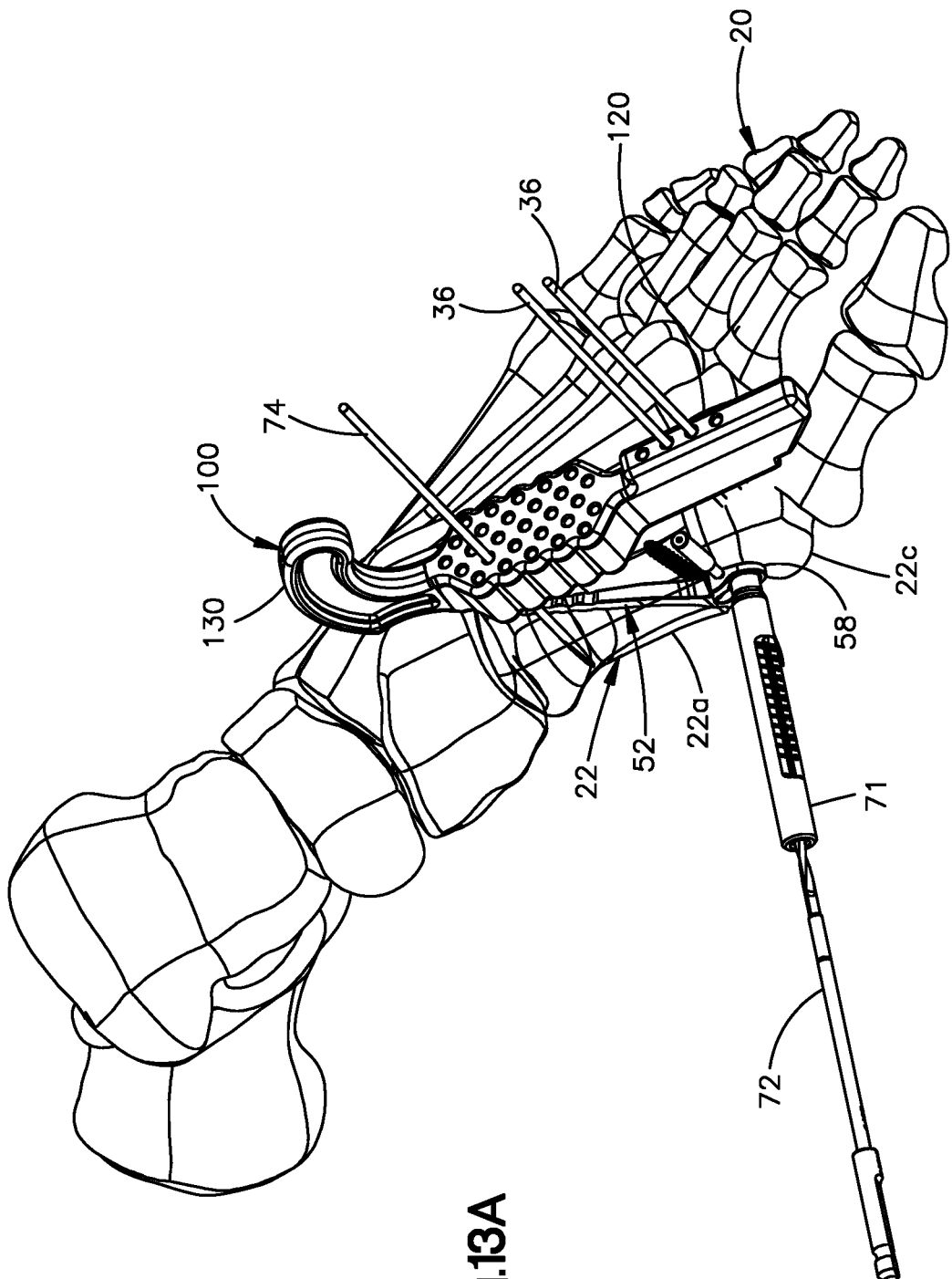
FIG. 13A is a perspective view of the patient's foot of FIG. 12C, but showing a drill guide positioned to drill a distal bone fastener hole through the implant and into the capital fragment of the first metatarsal.
Figure 13B:
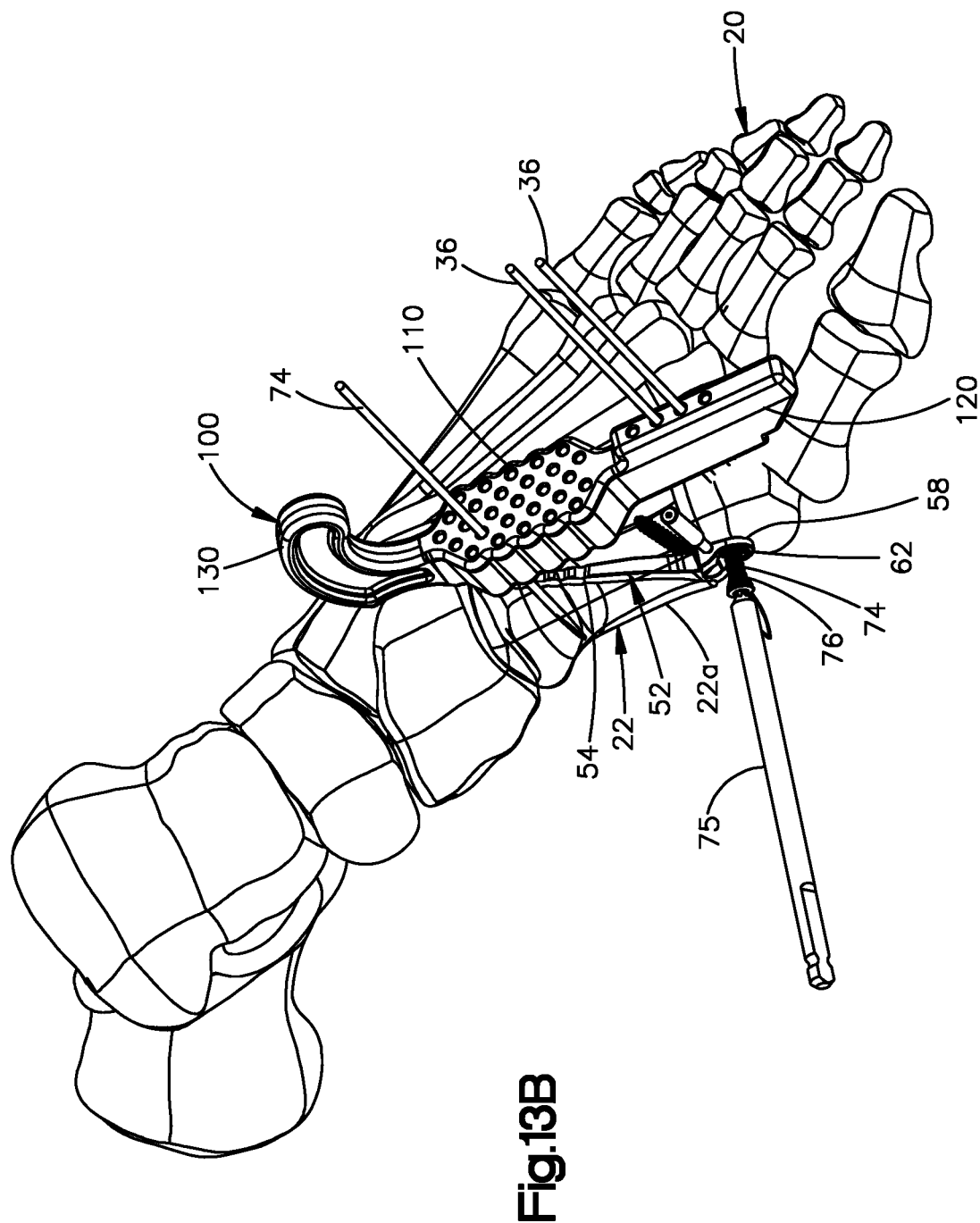
FIG. 13B is a perspective view of the patient's foot of FIG. 13A, showing the distal bone fastener being driven by a driver instrument through the implant and into the capital fragment of the first metatarsal.
Figure 13C:
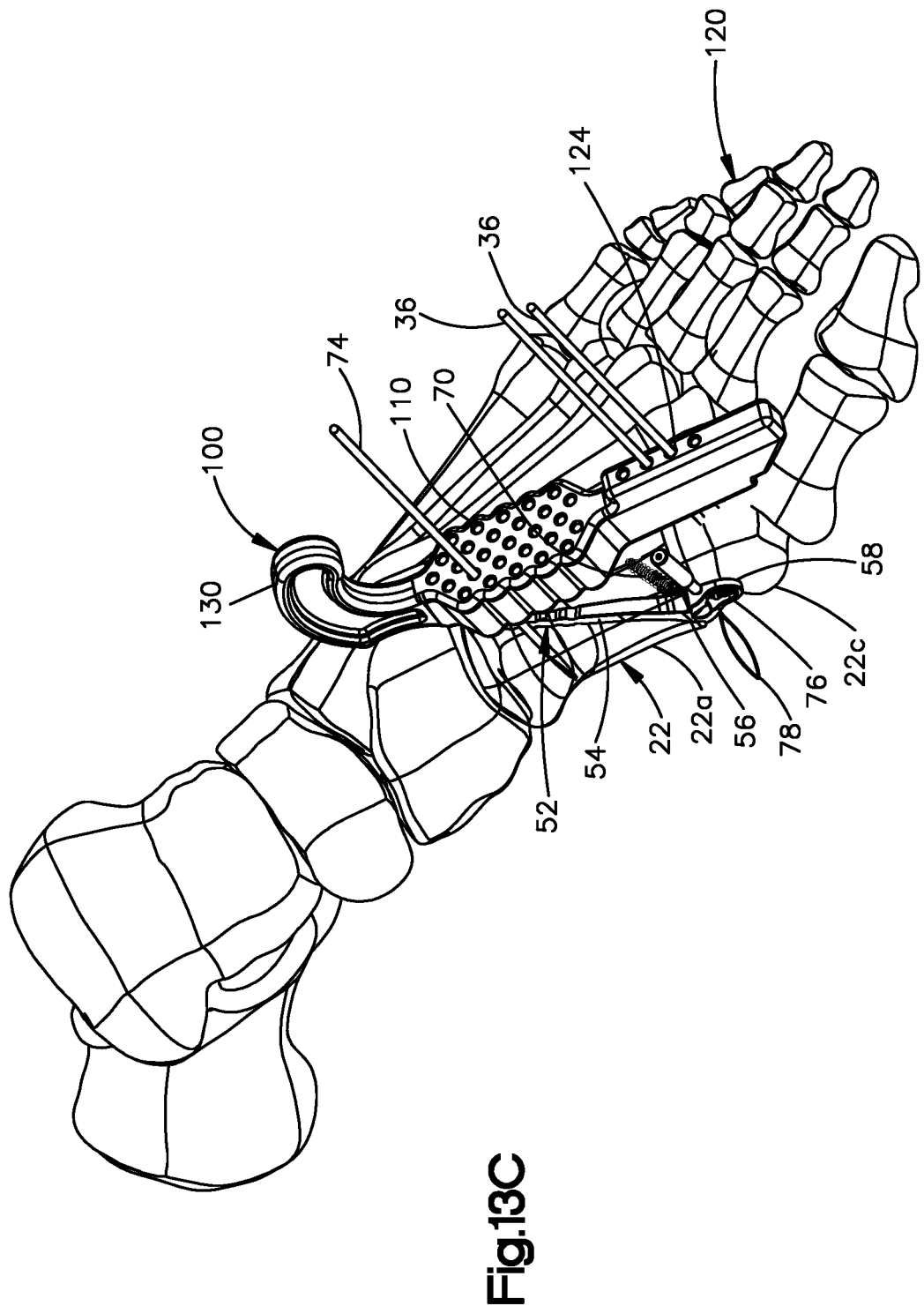
FIG. 13C is a perspective view of the patient's foot of FIG. 13B, showing the distal bone fastener fully seated in the implant and driven into the capital fragment of the first metatarsal, showing the driver instrument removed.

Referring now to FIGS. 13A-13C, once the capital fragment 22c has been moved to the aligned position by the at least one distal K-wire 36, the capital fragment 22c can be permanently fixed to the implant 52. In particular, as shown in FIG. 13A, a drill guide 71 can receive a drill 73 that can be driven through the distal fixation aperture 62 and into the capital fragment 22c of the metatarsal 22 so as to create a hole in the capital fragment 22c that will receive a bone fastener. The drill guide 71 can be supported by a handle such as the handle 68 described above with respect to FIG. 11A. As illustrated in FIGS. 13B-13C, a driver instrument 75 can drive a distal bone fastener 76 through the distal fixation aperture 62 and into the created hole in capital fragment 22c. In other examples, the proximal bone fastener 70 can be driven into the proximal portion 22a without first preparing the proximal portion 22a with the hole.

The surgical system can include the distal bone fastener 76. The central axis of the fixation aperture 62 can extend along a trajectory that is oriented substantially laterally or any suitable alternative direction into the capital fragment 22c. The distal bone fastener 76 can be driven along the central axis of the fixation aperture 62 through the distal fixation aperture 62 and into the capital fragment 22c. In one example, the distal bone fastener 76 can be configured as a distal bone screw configured in any manner as described above with respect to the proximal bone fastener 70 (see FIGS. 11A-11C). Thus, the distal bone fastener 76 can have a threaded shaft 74 that threadedly purchases with the capital fragment 22c. When the distal bone fastener 76 is seated against the implant 52 in the distal fixation aperture 62 and the shaft 74 is inserted into the capital fragment 22c, the implant 52 is secured and fixed to the capital fragment 22c with respect to relative movement. Thus, movement of the implant 52 relative to the capital fragment 22c is prevented. It should therefore be appreciated that the implant 52 is permanently fixed to each of the proximal portion 22a and the capital fragment 22c, such that movement of the capital fragment 22c with respect to the proximal portion 22a is prevented. It should be appreciated that any number of distal bone fasteners 72 can be driven through any number of distal fixation apertures 62 of the implant 52 and into the capital fragment 22c as desired. The head 58 can sit against the capital fragment 22c in some examples. In other examples, a drill or reamer can create a cavity in the capital fragment 22c that is aligned with head 58 such that the head 58 can be seated in the cavity when the head is secured to the capital fragment 22c. Thus, the head 58 can be recessed with respect to the outer surface of the capital fragment 22c.

With continuing reference to FIG. 13C, once the capital fragment 22c is permanently fixed to the proximal portion 22a in the aligned position, the angle of the proximal phalanx 24 with respect to the metatarsal 22 can be adjusted as desired. In particular, the implant 52 can include a loop 78 that can be made of suture, biocompatible metal, or any suitable alternative material. The loop 78 is configured to receive suture that extends through soft tissue of the foot so as to create a tension that adjusts the angle of the proximal phalanx 24 with respect to the metatarsal. The suture can be tied off so as to maintain the angle as desired. Adjustment of the angle of the proximal phalanx 24 using a suture as shown in FIGS. 11A-11E and related description in U.S. Patent Publication No. 2021/0038260, the entirety of which is incorporated by reference.

Figure 14:
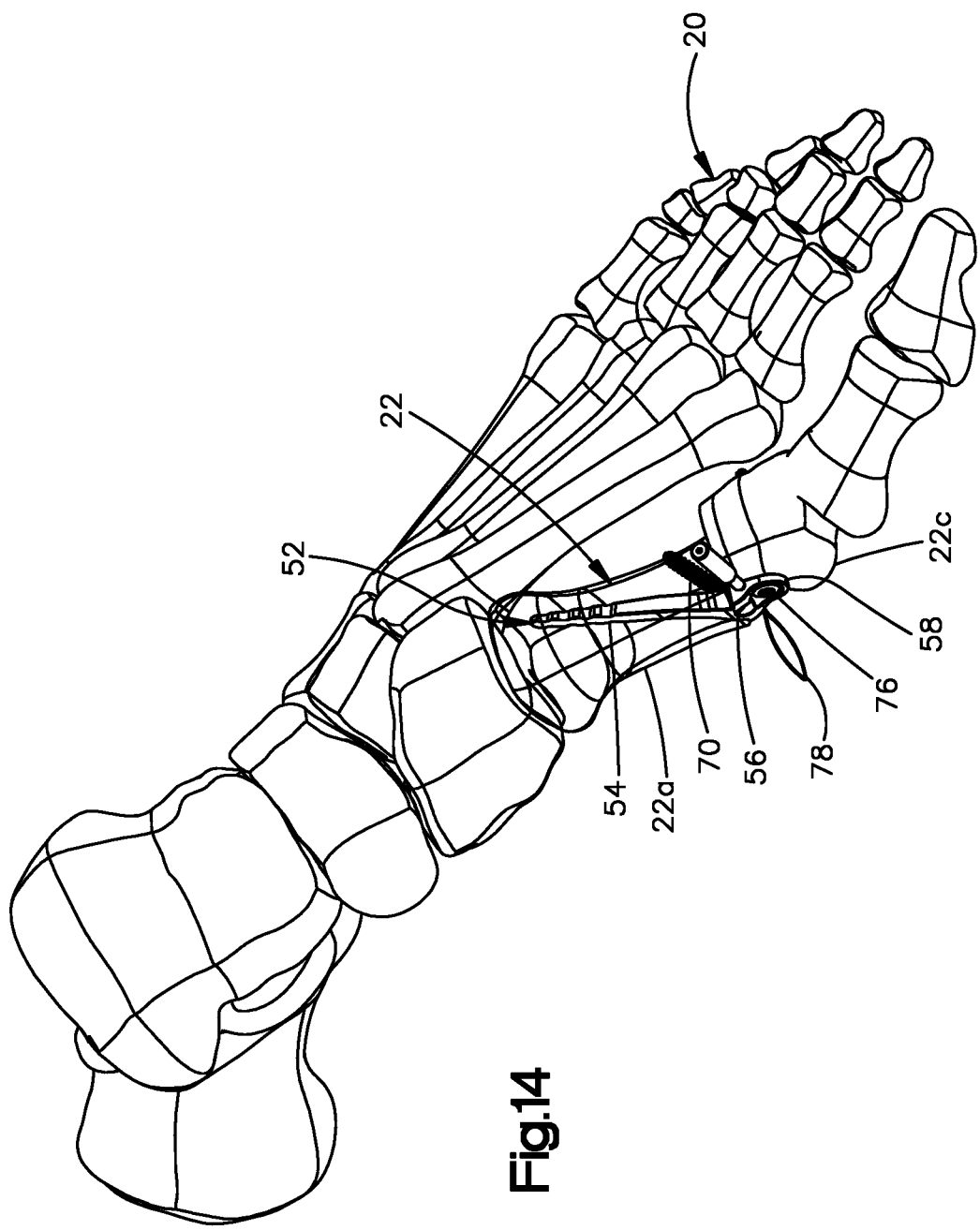
FIG. 14 is a perspective view of the patient's foot of FIG. 13C but upon completion of the surgical bunion correction procedure, showing the capital fragment guide removed, and further showing the two K-wires and the third K-wire removed.

Once the implant 52 has been permanently fixed to the capital fragment 22c, capital fragment guide 100 can be removed from the proximal and distal K-wires 74 and 36, respectively, the proximal K-wire 74 can be removed from the proximal portion 22a of the metatarsal 22, and the distal K-wire 36 can be removed from the capital fragment 22c as shown in FIG. 14. The incision can then be closed in the usual manner.

Certain Terminology

Terms of orientation used herein, such as "top," "bottom," "proximal," "distal," "longitudinal," "lateral," and "end," are used in the context of the illustrated example. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to also include any suitable structure with a cross-sectional region that can be measured from side-to-side. Terms relating to shapes generally, such as "circular," "cylindrical," "semi-circular," or "semi-cylindrical" or any related or similar terms, are not required to conform strictly to the mathematical definitions of circles or cylinders or other structures, but can encompass structures that are reasonably close approximations.

Conditional language, such as "can," "could," "might," or "may," unless specifically stated otherwise, or otherwise understood within the context as used, is generally intended to convey that certain examples include or do not include, certain features, elements, and/or steps. Thus, such conditional language is not generally intended to imply that features, elements, and/or steps are in any way required for one or more examples.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

The terms "approximately," "about," and "substantially" as used herein represent an amount close to the stated amount that still performs a desired function or achieves a desired result. For example, in some examples as the context may dictate, the terms "substantially," "approximately," and "about" as used with respect to a dimension, direction, shape, or other parameter can include the stated parameter and differences from the stated parameter up to +/−10%, including 9%, including 8%, including 7%, including 6%, including 5%, including 4%, including 3%, including 2%, including 1%. The term "generally" as used herein represents a value, amount, or characteristic that predominantly includes or tends toward a particular value, amount, or characteristic. As an example, in certain examples, as the context may dictate, the term "generally parallel" can refer to something that departs from exactly parallel by less than or equal to 20 degrees. All ranges are inclusive of endpoints.

Several illustrative examples of surgical devices and related methods have been disclosed. Although this disclosure has been described in terms of certain illustrative examples and uses, other examples and other uses, including examples and uses which do not provide all of the features and advantages set forth herein, are also within the scope of this disclosure. Components, elements, features, acts, or steps can be arranged or performed differently than described and components, elements, features, acts, or steps can be combined, merged, added, or left out in various examples. All possible combinations and subcombinations of elements and components described herein are intended to be included in this disclosure. No single feature or group of features is necessary or indispensable.

Certain features that are described in this disclosure in the context of separate implementations can also be implemented in combination in a single implementation. Conversely, various features that are described in the context of a single implementation also can be implemented in multiple implementations separately or in any suitable subcombination. Moreover, although features may be described above as acting in certain combinations, one or more features from a claimed combination can in some cases be excised from the combination, and the combination may be claimed as a subcombination or variation of a subcombination.

Any portion of any of the steps, processes, structures, and/or devices disclosed or illustrated in one example in this disclosure can be combined or used with (or instead of) any other portion of any of the steps, processes, structures, and/or devices disclosed or illustrated in a different example or flowchart. The examples described herein are not intended to be discrete and separate from each other. Combinations, variations, and some implementations of the disclosed features are within the scope of this disclosure.

While operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Additionally, the operations may be rearranged or reordered in some implementations. Also, the separation of various components in the implementations described above should not be understood as requiring such separation in all implementations, and it should be understood that the described components and systems can generally be integrated together in a single product or packaged into multiple products. Additionally, some implementations are within the scope of this disclosure.

Further, while illustrative examples have been described, any examples having equivalent elements, modifications, omissions, and/or combinations are also within the scope of this disclosure. Moreover, although certain aspects, advantages, and novel features are described herein, not necessarily all such advantages may be achieved in accordance with any particular example. For example, some examples within the scope of this disclosure achieve one advantage, or a group of advantages, as taught herein without necessarily achieving other advantages taught or suggested herein. Further, some examples may achieve different advantages than those taught or suggested herein.

Some examples have been described in connection with the accompanying drawings. The figures are drawn and/or shown to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various examples can be used in all other examples set forth herein. Additionally, any methods described herein may be practiced using any device suitable for performing the recited steps.

For purposes of summarizing the disclosure, certain aspects, advantages and features of the inventions have been described herein. Not all, or any such advantages are necessarily achieved in accordance with any particular example of the inventions disclosed herein. No aspects of this disclosure are essential or indispensable. In many examples, the devices, systems, and methods may be configured differently than illustrated in the figures or description herein. For example, various functionalities provided by the illustrated modules can be combined, rearranged, added, or deleted. In some implementations, additional or different processors or modules may perform some or all of the functionalities described with reference to the examples described and illustrated in the figures. Many implementation variations are possible. Any of the features, structures, steps, or processes disclosed in this specification can be included in any example.

In summary, various examples of surgical devices and related methods have been disclosed. This disclosure extends beyond the specifically disclosed examples to other alternative examples and/or other uses of the examples, as well as to certain modifications and equivalents thereof. Moreover, this disclosure expressly contemplates that various features and aspects of the disclosed examples can be combined with, or substituted for, one another. Accordingly, the scope of this disclosure should not be limited by the particular disclosed examples described above, but should be determined only by a fair reading of the claims.

What is claimed is:

1. A guide configured to adjust a first portion of a metatarsal and a second portion of bone that includes a capital fragment of the metatarsal that has been surgically separated from the first portion of the metatarsal, the guide comprising:
   a body portion that defines a bone-facing inner surface and an outer surface opposite the inner surface, wherein the guide defines a plurality of body portion apertures that extend through the body portion from the outer surface to the inner surface;
   an alignment portion that extends from the body portion, the alignment portion defining a bone-facing inner surface and an outer surface opposite the inner surface, wherein the guide defines a plurality of alignment apertures that extend through the alignment portion from the outer surface of the alignment portion to the inner surface of the alignment portion; and a handle that extends from the body portion, such that the alignment portion and the handle extend from opposite ends of the body portion, wherein the guide is sized such that at least one of the alignment apertures is capable of being aligned with the second portion, and wherein at least one of the alignment apertures is configured to receive a temporary distal fixation device to be inserted into the second portion, wherein the guide is sized to align at least one of the body portion apertures with the first portion while at least one of the plurality of alignment apertures is aligned with the second portion, and wherein at least one of the body portion apertures is configured to receive a temporary proximal fixation device to be inserted into the first portion.

2. The guide of claim 1, wherein the plurality of alignment apertures are configured to receive respective temporary distal fixation devices that are each to be inserted into the second portion.

3. The guide of claim 1, wherein the temporary proximal and distal fixation devices comprise k-wires.

4. The guide of claim 1, wherein the alignment apertures and the body portion apertures extend along respective central axes that are parallel to each other.

5. The guide of claim 1, wherein the alignment apertures extend along respective central axes that are parallel to each other, and the body portion apertures extend along respective central axes that are parallel to each other and angularly offset with respect to the alignment apertures.

6. The guide of claim 1, wherein the inner surface of the body portion and the outer surface of the body portion are planar and parallel to each other.

7. The guide of claim 1, wherein the alignment portion has a height, the body portion has a height, and the height of the alignment portion is greater than the height of the body portion.

8. The guide of claim 1, wherein the handle includes a grip section.

9. The guide of claim 8, wherein the grip section extends above the outer surface of the body portion in a direction from the inner surface toward the outer surface.

10. The guide of claim 1, wherein the body portion apertures comprise a central section of body portion apertures that are aligned with each other along a longitudinal direction, and the alignment apertures are aligned in a column that is aligned with the central section of body portion apertures.

11. The guide of claim 10, wherein the body portion apertures further comprisd a first side section of apertures and a second side section of apertures, wherein the first side section of apertures is disposed between the central section and a first external side of the body portion, and the second side section of apertures is disposed between the central section and a second external side of the body portion that is opposite the first external side along a lateral direction that is perpendicular to the longitudinal direction, wherein the inner surface of the body portion is opposite the outer surface of the body portion along a transverse direction that is perpendicular to each of the lateral direction and the longitudinal direction.

12. A surgical system comprising:
the guide of claim 1;
a cut guide configured to receive a cutting instrument that cuts through the metatarsal so as to separate the second portion from the first portion; and
an implant.

13. A method for adjusting alignment between a first portion of a bone and a second portion of the bone, the method comprising:
aligning at least one alignment aperture of an alignment portion of a guide with the second portion of the bone;
after the aligning step, driving at least one distal temporary fixation member through the at least one alignment aperture and into the second portion of the bone;
resecting the bone to separate the second portion from the first portion, such that the second portion of the bone defines a separated second portion, wherein the first portion of the bone comprises a first portion of a metatarsal, and the second portion comprises a capital fragment of the metatarsal;
permanently fixing an implant to the first portion;
using a handle of the guide to move the alignment portion, thereby moving the at least one distal temporary fixation member with respect to the first portion so as to correspondingly move and reposition the separated second portion with respect to the first portion, wherein the guide further comprises a body portion, and the handle and the alignment portion extend from opposite ends of the body portion;
permanently fixing the implant to the separated second portion; and
after the permanently fixing steps, removing the at least one distal temporary fixation member from the separated second portion.

14. The method of claim 13, wherein the aligning step further comprises aligning at least one aperture of the body portion with the first portion of the bone, and the driving step comprises driving a pair of distal temporary fixation members percutaneously through alignment apertures and into the second portion.

15. The method of claim 14, further comprising the step of, between the moving the at least one distal temporary fixation member step and the second permanently fixing step, driving a proximal temporary fixation member percutaneously through a body portion aperture and into the first portion.

16. The method of claim 15, wherein the method further comprises removing the proximal temporary fixation member from the first portion.

17. The method of claim 16, wherein the proximal temporary fixation member comprises a proximal K-wire.

18. The method of claim 14, wherein the at least one alignment aperture comprises a plurality of alignment apertures, the at least one distal temporary fixation member comprises a plurality of distal temporary fixation members, the method further comprising the step of placing the guide over the distal temporary fixation members such that the distal temporary fixation members are received in corresponding ones of the plurality of alignment apertures, and the moving step comprises moving the guide with respect to the first portion, and positioning the guide external of a human body that contains the bone.

19. The method of claim 18, wherein the moving step corrects a bunion.

20. The method of claim 13, further comprising inserting the implant into a medullary canal of the first portion.

* * * * *